United States Patent
Kuroda et al.

(10) Patent No.: US 11,612,306 B2
(45) Date of Patent: Mar. 28, 2023

(54) SURGICAL ARM SYSTEM AND SURGICAL ARM CONTROL SYSTEM

(71) Applicant: Sony Corporation, Tokyo (JP)

(72) Inventors: Yohei Kuroda, Tokyo (JP); Jun Arai, Tokyo (JP); Masaru Usui, Tokyo (JP); Takeshi Maeda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 373 days.

(21) Appl. No.: 16/758,864

(22) PCT Filed: Oct. 24, 2018

(86) PCT No.: PCT/JP2018/039539
§ 371 (c)(1),
(2) Date: Apr. 24, 2020

(87) PCT Pub. No.: WO2019/087904
PCT Pub. Date: May 9, 2019

(65) Prior Publication Data
US 2021/0369351 A1 Dec. 2, 2021

(30) Foreign Application Priority Data
Nov. 1, 2017 (JP) .............................. JP2017-211783

(51) Int. Cl.
*B25J 9/16* (2006.01)
*A61B 1/00* (2006.01)
(Continued)

(52) U.S. Cl.
CPC ...... *A61B 1/00149* (2013.01); *A61B 1/00006* (2013.01); *A61B 1/00009* (2013.01);
(Continued)

(58) Field of Classification Search
CPC ................ A61B 34/20; A61B 1/00006; A61B 1/00149; A61B 34/30; A61B 2034/2065;
(Continued)

(56) References Cited

U.S. PATENT DOCUMENTS 5,673,367 A * 9/1997 Buckley ................ B25J 9/1612
706/23
6,471,637 B1 * 10/2002 Green ................ A61B 1/00045
600/137
(Continued)

FOREIGN PATENT DOCUMENTS

| CN | 101449962 A | * | 6/2009 | ........... A61B 1/0669 |
| CN | 101351145 B | * | 8/2010 | ......... A61B 1/00158 |

(Continued)

OTHER PUBLICATIONS

"User interface of force-controlled arm for endoscopic surgery;" Kasai et al.; "2017 IEEE/RSJ International Conference on Intelligent Robots and Systems (IROS) (pp. 6477-6483);" Jan. 19, 2018. (Year: 2018).*

(Continued)

*Primary Examiner* — Khoi H Tran
*Assistant Examiner* — Jorge O Peche
(74) *Attorney, Agent, or Firm* — Xsensus LLP

(57) ABSTRACT

[Problem] To prevent sight of an observation target from being lost from a visual field of a monitor.
[Solution] A surgical arm system includes: an articulated arm in which a plurality of joints is rotatably connected by a plurality of links and which is capable of supporting an oblique-viewing endoscope at a tip; and a control system which controls the articulated arm to change a position and a posture of the oblique-viewing endoscope. The control system controls at least one of a rotation speed and a movement speed of the oblique-viewing endoscope in a
(Continued)

visual field imaged through the oblique-viewing endoscope based on a position of the observation target in the visual field.

15 Claims, 20 Drawing Sheets

(51) Int. Cl.
*A61B 34/20* (2016.01)
*A61B 34/30* (2016.01)
(52) U.S. Cl.
CPC .............. *A61B 34/20* (2016.02); *A61B 34/30* (2016.02); *B25J 9/1697* (2013.01); *A61B 2034/2065* (2016.02); *A61B 2034/301* (2016.02)
(58) Field of Classification Search
CPC .......... A61B 2034/301; A61B 1/00009; A61B 1/00179; B25J 9/1697
See application file for complete search history.

(56) References Cited

U.S. PATENT DOCUMENTS

| | | | | |
|---|---|---|---|---|
| 6,915,283 | B2 * | 7/2005 | Tani | G05B 13/027 706/30 |
| 10,368,725 | B2 * | 8/2019 | Uemori | A61B 1/00045 |
| 2002/0085272 | A1 * | 7/2002 | Tomioka | G02B 23/2484 359/362 |
| 2002/0161280 | A1 * | 10/2002 | Chatenever | A61B 1/042 600/137 |
| 2006/0084840 | A1 * | 4/2006 | Hoeg | A61B 1/042 600/117 |
| 2011/0306834 | A1 * | 12/2011 | Schrader | G02B 23/2484 600/109 |
| 2012/0083947 | A1 * | 4/2012 | Anderson | G08G 1/166 701/1 |
| 2015/0351712 | A1 * | 12/2015 | Ohishi | A61B 6/4014 378/62 |
| 2016/0263749 | A1 * | 9/2016 | Ogata | B25J 9/126 |
| 2017/0080574 | A1 * | 3/2017 | Kuroda | A61B 34/35 |
| 2017/0135563 | A1 * | 5/2017 | Uemori | H04N 5/23238 |
| 2018/0029226 | A1 * | 2/2018 | Dani | G06V 10/10 |
| 2018/0079076 | A1 * | 3/2018 | Toda | G06N 5/022 |
| 2018/0104013 | A1 * | 4/2018 | Hamamoto | A61B 1/0052 |
| 2019/0262090 | A1 * | 8/2019 | Kokubo | A61B 1/00149 |
| 2019/0274524 | A1 * | 9/2019 | Nagao | A61B 1/042 |
| 2019/0281233 | A1 * | 9/2019 | Yorozu | H04N 5/2251 |
| 2019/0365489 | A1 * | 12/2019 | Kasai | A61B 1/00188 |
| 2020/0046208 | A1 * | 2/2020 | Kasai | A61B 1/3132 |
| 2020/0060523 | A1 * | 2/2020 | Matsuda | A61B 1/00045 |
| 2020/0084379 | A1 * | 3/2020 | Ikeda | A61B 1/3132 |
| 2020/0160989 | A1 * | 5/2020 | Korehisa | A61B 90/361 |
| 2020/0178760 | A1 * | 6/2020 | Kashima | A61L 2/07 |
| 2021/0007593 | A1 * | 1/2021 | Arai | A61B 1/0661 |
| 2021/0015346 | A1 * | 1/2021 | Kuroda | A61B 1/0661 |
| 2021/0019921 | A1 * | 1/2021 | Yoshida | G06T 11/001 |
| 2021/0145254 | A1 * | 5/2021 | Shekhar | G02B 23/2453 |
| 2021/0169305 | A1 * | 6/2021 | Fukazawa | G06T 5/008 |
| 2021/0369092 | A1 * | 12/2021 | Arai | A61B 1/00149 |
| 2021/0369351 | A1 * | 12/2021 | Kuroda | G02B 21/36 |
| 2021/0382280 | A1 * | 12/2021 | Hosono | G02B 27/0012 |
| 2022/0008156 | A1 * | 1/2022 | Tomatsu | G02B 23/2469 |
| 2022/0022728 | A1 * | 1/2022 | Kuwayama | G01N 21/17 |
| 2022/0167083 | A1 * | 5/2022 | Koizumi | H04R 5/027 |
| 2022/0174231 | A1 * | 6/2022 | Akebono | H03F 3/34 |
| 2022/0192777 | A1 * | 6/2022 | Kuroda | A61B 90/37 |

FOREIGN PATENT DOCUMENTS

| | | | | |
|---|---|---|---|---|
| CN | 109922933 A | * | 6/2019 | .............. A61B 1/00 |
| CN | 110325093 A | * | 10/2019 | ......... A61B 1/00149 |
| CN | 110461208 A | * | 11/2019 | ......... A61B 1/00006 |
| CN | 110678142 A | * | 1/2020 | .............. A61B 34/30 |
| CN | 111278344 A | * | 6/2020 | .............. A61B 1/00 |
| CN | 113645919 A | * | 11/2021 | ......... A61B 1/00006 |
| CN | 114340469 A | * | 4/2022 | |
| CN | 114340470 A | * | 4/2022 | |
| DE | 112018001058 T5 | * | 11/2019 | .............. A61B 1/00 |
| DE | 112019004308 T5 | * | 5/2021 | ......... A61B 1/00009 |
| DE | 112019004340 T5 | * | 5/2021 | ......... A61B 1/00006 |
| EP | 3 590 405 A1 | | 1/2020 | |
| EP | 3 590 406 A1 | | 1/2020 | |
| EP | 3733047 A1 | * | 11/2020 | ............ A61B 90/361 |
| EP | 3179897 B1 | * | 1/2021 | ......... A61B 1/00009 |
| EP | 3952304 A1 | * | 2/2022 | ............ G06F 3/0484 |
| EP | 3992690 A1 | * | 5/2022 | |
| JP | H05337118 A | | 12/1993 | |
| JP | H09-028663 A | | 2/1997 | |
| JP | 2000051149 A | * | 2/2000 | |
| JP | 2004173972 A | * | 6/2004 | |
| JP | 2004173973 A | * | 6/2004 | |
| JP | 2004-275203 A | | 10/2004 | |
| JP | 2006-218027 A | | 8/2006 | |
| JP | 4382894 B2 | | 12/2009 | |
| JP | 2017093818 A | | 6/2011 | |
| JP | 2016-524487 A | | 8/2016 | |
| JP | WO2014157645 A1 | * | 2/2017 | |
| JP | 2019084334 A | * | 6/2019 | ......... A61B 1/00149 |
| JP | WO2019087904 A1 | * | 12/2020 | |
| JP | 2021521989 A | * | 8/2021 | |
| KR | 20210005682 A | * | 1/2021 | |
| WO | WO-2016072059 A1 | * | 5/2016 | ......... A61B 1/00009 |
| WO | 2017/154557 A1 | | 9/2017 | |
| WO | 2017/163407 A1 | | 9/2017 | |
| WO | WO-2018159328 A1 | * | 9/2018 | ......... A61B 1/00149 |
| WO | WO-2019012817 A1 | * | 1/2019 | .............. G06T 15/20 |
| WO | WO-2019087904 A1 | * | 5/2019 | ............... A61B 1/00 |
| WO | WO-2019087934 A1 | * | 5/2019 | ......... A61B 1/00149 |
| WO | WO-2019181149 A1 | * | 9/2019 | ......... A61B 1/00126 |
| WO | WO-2020075773 A1 | * | 4/2020 | ......... A61B 1/00009 |
| WO | WO-2020196338 A1 | * | 10/2020 | ......... A61B 1/00006 |
| WO | WO-2021006228 A1 | * | 1/2021 | ......... A61B 1/00009 |
| WO | WO-2021171465 A1 | * | 9/2021 | |
| WO | WO-2022019318 A2 | * | 1/2022 | |
| WO | WO-2022054847 A1 | * | 3/2022 | |

OTHER PUBLICATIONS

"Human Interface and Control of a Robotic Endoscope Holder Based on an AR Approach;" Kuo et al., 2020 International Automatic Control Conference (CACS) (pp. 1-6); Nov. 4, 2020. (Year: 2020).*

"FlexiVision: Teleporting the Surgeon's Eyes via Robotic Flexible Endoscope and Head-Mounted Display;" Qian et al.; 2020 IEEE/RSJ International Conference on Intelligent Robots and Systems (IROS) (pp. 3281-3287); Oct. 24, 2020. (Year: 2020).*

"Insertable stereoscopic 3D surgical imaging device with pan and tilt;" Hu et al.; 2008 2nd IEEE RAS & EMBS International Conference on Biomedical Robotics and Biomechatronics (pp. 311-316); Mar. 9, 2009. (Year: 2009).*

International Search Report and Written Opinion dated Jan. 22, 2019 for PCT/JP2018/039539 filed on Oct. 24, 2018, 7 pages including English Translation of the International Search Report.

* cited by examiner

SURGICAL ARM SYSTEM AND SURGICAL ARM CONTROL SYSTEM

CROSS-REFERENCE TO RELATED APPLICATIONS

The present application is based on PCT filing PCT/JP2018/039539, filed Oct. 24, 2018, which claims priority to JP 2017-211783, filed Nov. 1, 2017, the entire contents of each are incorporated herein by reference.

FIELD

The present disclosure relates to a control device for an oblique-viewing endoscope and a medical system.

BACKGROUND

In the related art, for example, in Patent Document 1 below, a technology is described that assumes that an endoscope image in which the up, down, left, and right directions of an endoscope image coincide with the up, down, left, and right operation directions of an operator can be displayed on a monitor so as not to cause a sense of incongruity during operation.

CITATION LIST

Patent Literature

Patent Literature 1: JP 2006-218027 A

SUMMARY

Technical Problem

In recent years, an oblique-viewing endoscope has been used as a rigid scope inserted into the human body. However, the oblique-viewing rotation by the oblique-viewing endoscope is made with respect to the scope axis, and thus there is a problem that the visual field after the rotation is less intuitive compared to the simple horizontal or vertical movement. For this reason, there have been problems such as the observation target being out of the visual field of the screen due to the oblique-viewing rotation, and losing the sight of the instrument shown in the visual field.

Therefore, it has been demanded that the sight of the observation target is not lost from the visual field of the monitor image.

Solution to Problem

According to the present disclosure, a surgical arm system is provided that includes: an articulated arm in which a plurality of joints is rotatably connected by a plurality of links and which is capable of supporting an oblique-viewing endoscope at a tip; and a control system which controls the articulated arm to change a position and a posture of the oblique-viewing endoscope, wherein the control system controls at least one of a rotation speed and a movement speed of the oblique-viewing endoscope in a visual field imaged through the oblique-viewing endoscope based on a position of an observation target in the visual field.

Moreover, according to the present disclosure, a surgical arm control system is provided which controls an articulated arm in which a plurality of joints is rotatably connected by a plurality of links and which is capable of supporting an oblique-viewing endoscope at a tip, and controls the articulated arm to change a position and a posture of the oblique-viewing endoscope, wherein at least one of a rotation speed and a movement speed of the oblique-viewing endoscope is controlled in a visual field imaged through the oblique-viewing endoscope based on a position of an observation target in the visual field.

Advantageous Effects of Invention

According to the present disclosure, it is possible to prevent the sight of an observation target from being lost from the visual field of a monitor image.

Note that the above effects are not necessarily limited, and any of the effects shown in the present specification or other effects that can be grasped from the present specification may be exerted together with or in place of the above effects.

DESCRIPTION OF EMBODIMENTS

Figure 1:
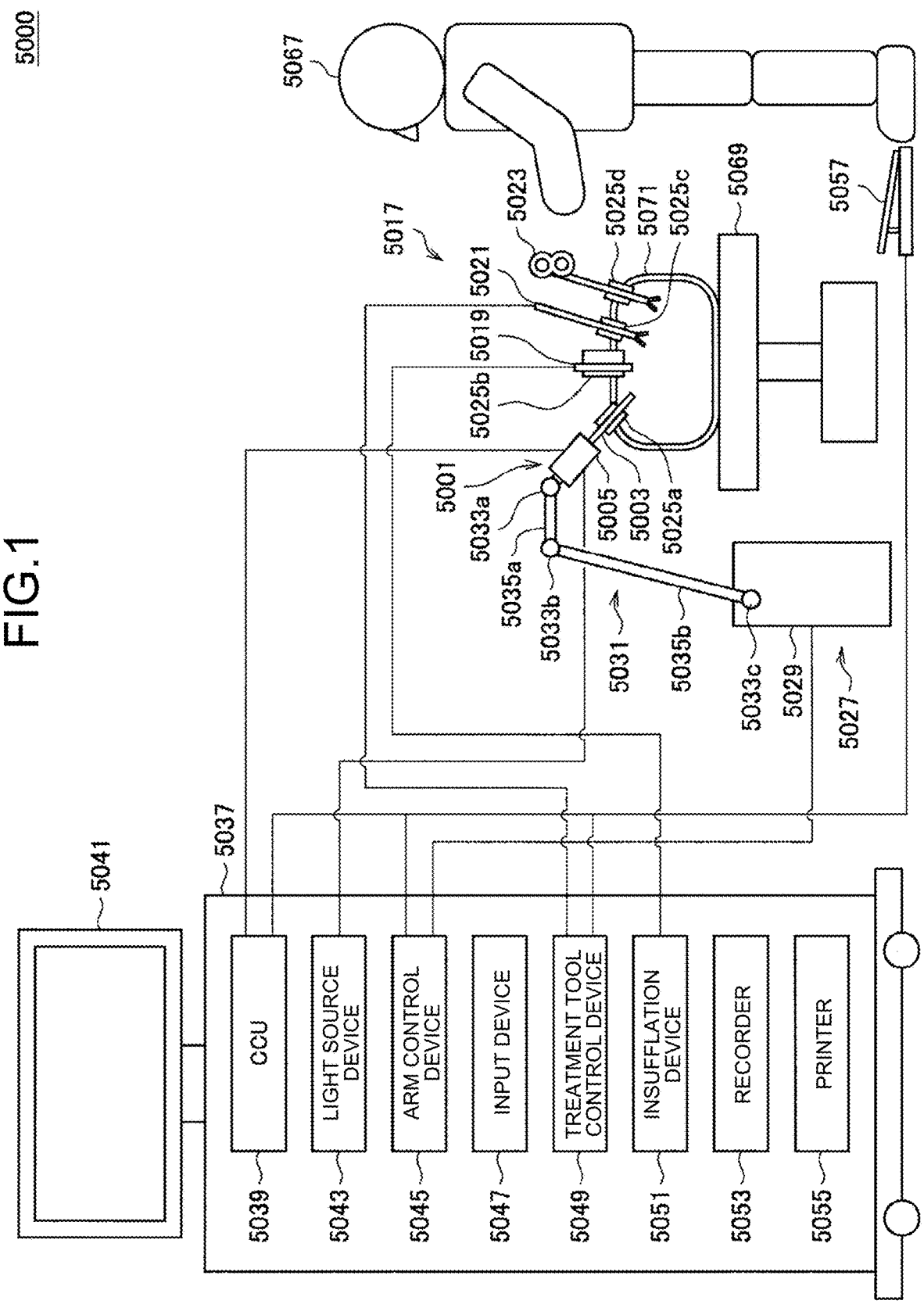
FIG. 1 is a diagram illustrating an example of a schematic configuration of an endoscopic surgery system to which a medical support arm device according to the present disclosure can be applied.

Hereinafter, preferred embodiments of the present disclosure will be described in detail with reference to the accompanying drawings. In addition, in this specification and drawing, constituent elements having substantially the same functional configuration are denoted by the same reference numerals, and redundant description is omitted.

The description will be made in the following order.
1. Basic configuration
  1.1. Configuration example of endoscope system
  1.2. Specific configuration example of medical support arm device
  1.3. Configuration example of control device
2. Oblique-viewing rotation operation and follow-up operation to observation target by the oblique-viewing endoscope
  2.1. Rotation operation of oblique-viewing endoscope
  2.2. Change of oblique-viewing rotation speed according to distance from center of visual field
  2.3. Follow-up operation to observation target
  2.4. Configuration example of control unit for oblique-viewing rotation operation and follow-up operation
  2.5. Details of follow-up operation
  2.6. Specific example of follow-up operation
3. Example of holding unit that independently controls rotation of oblique-viewing endoscope
4. Summary <<1. Basic Configuration>>

First, a basic configuration of an endoscope system according to an embodiment of the present disclosure will be described with reference to FIGS. 1 to 4.

<1.1. Configuration Example of Endoscope System>

FIG. 1 is a diagram illustrating an example of a schematic configuration of an endoscopic surgery system 5000 to which the technology according to the present disclosure can be applied. FIG. 1 illustrates an aspect in which an operator (doctor) 5067 is performing a surgery on a patient 5071 on a patient bed 5069 using the endoscopic surgery system 5000. As illustrated, the endoscopic surgery system 5000 includes an endoscope 5001, other surgical tools 5017, a support arm device 5027 for supporting the endoscope 5001, and a cart 5037 equipped with various devices for endoscopic surgery.

In endoscopic surgery, a plurality of cylindrical opening instruments called trocars 5025a to 5025d are punctured into the abdominal wall instead of cutting and opening the abdominal wall. Then, a lens barrel 5003 of the endoscope 5001 and other surgical tools 5017 are inserted into the body cavity of the patient 5071 from the trocars 5025a to 5025d. In the illustrated example, as other surgical tools 5017, an insufflation tube 5019, an energy treatment tool 5021, and forceps 5023 are inserted into the body cavity of the patient 5071. The energy treatment tool 5021 is a treatment device that performs incision and exfoliation of tissue, sealing of blood vessels, and the like by using high-frequency current and ultrasonic vibration. However, the illustrated surgical tool 5017 is merely an example, and various surgical tools, which are generally used in endoscopic surgery, such as a set and a retractor may be used as the surgical tool 5017.

An image of the operation site in the body cavity of the patient 5071 captured by the endoscope 5001 is displayed on a display device 5041. The operator 5067 performs a process to excise an affected part using the energy treatment tool 5021 and the forceps 5023 while viewing the image of the operation site displayed on the display device 5041 in real time, for example. Although not illustrated, the insufflation tube 5019, the energy treatment tool 5021, and the forceps 5023 are supported by the operator 5067, an assistant, or the like during surgery.

(Support Arm Device)

The support arm device 5027 includes an arm unit 5031 extending from a base unit 5029. In the illustrated example, the arm unit 5031 includes joints 5033a, 5033b, 5033c, and links 5035a and 5035b, and is driven by control from the arm control device 5045. The endoscope 5001 is supported by the arm unit 5031, and the position and posture of the endoscope are controlled. Thereby, the position of the endoscope 5001 can be fixed stably.

(Endoscope)

The endoscope 5001 includes the lens barrel 5003 of which the area having a predetermined length from the tip is inserted into the body cavity of the patient 5071 and a camera head 5005 connected to the proximal end of the lens barrel 5003. In the illustrated example, the endoscope 5001 configured as a so-called rigid scope having the rigid lens barrel 5003 is illustrated, but the endoscope 5001 may be configured as a so-called flexible endoscope having a soft lens barrel 5003.

An opening to which an objective lens is fitted is provided at the tip of the lens barrel 5003. A light source device 5043 is connected to the endoscope 5001, the light generated by the light source device 5043 is guided to the tip of the lens barrel by a light guide extending inside the lens barrel 5003, and the light is emitted toward the observation target in the body cavity of the patient 5071 through the objective lens. Note that the endoscope 5001 is an oblique-viewing endoscope.

An optical system and an imaging element are provided inside the camera head 5005, and the reflected light (observation light) from the observation target is condensed on an imaging element by the optical system. The observation light is photoelectrically converted by the imaging element, and an electric signal corresponding to the observation light, that is, an image signal corresponding to the observation image is generated. The image signal is transmitted to a camera control unit (CCU) 5039 as RAW data. Incidentally, the camera head 5005 has a function of adjusting the magnification and the focal length by appropriately driving the optical system.

Note that the camera head 5005 may be provided with a plurality of imaging elements in order to support, for example, stereoscopic viewing (3D display). In this case, a plurality of relay optical systems are provided inside the lens barrel 5003 to guide observation light to each of the plurality of imaging elements.

(Various Devices Mounted on Cart)

The CCU 5039 is configured by a central processing unit (CPU), a graphics processing unit (GPU), and the like, and controls the operations of the endoscope 5001 and the display device 5041 in an integrated manner. Specifically, the CCU 5039 performs various types of image processing for displaying an image based on the image signal, such as a development process (demosaic process), on the image signal received from the camera head 5005. The CCU 5039 provides the image signal subjected to the image process to the display device 5041. Also, the CCU 5039 transmits a control signal to a camera head 5005, and controls the driving of the camera head. The control signal may include information on imaging conditions such as a magnification and a focal length.

The display device 5041 displays an image based on the image signal and subjected to the image process by the CCU 5039 under the control of the CCU 5039. For example, when the endoscope 5001 supports shooting at a high resolution such as 4K (3840 horizontal pixels×2160 vertical pixels) or 8K (7680 horizontal pixels×4320 vertical pixels), and/or if the endoscope supports 3D display, a device capable of high-resolution display and/or a device capable of 3D display may be used as the display device 5041 in response thereto. In the case of shooting at a high resolution such as 4K or 8K, the use of a display device 5041 having a size of 55 inches or more can provide a more immersive feeling. Further, a plurality of display devices 5041 having different resolutions and sizes may be provided depending on the application.

The light source device 5043 includes a light source such as a light emitting diode (LED) and supplies the endoscope 5001 with irradiation light when imaging the operation site.

The arm control device 5045 is configured by a processor such as a CPU, and operates according to a predetermined program to control the driving of the arm unit 5031 of the support arm device 5027 according to a predetermined control method.

The input device 5047 is an input interface for the endoscopic surgery system 5000. The user can input various information and input instructions to the endoscopic surgery system 5000 via the input device 5047.

For example, the user inputs, via the input device 5047, various types of information related to surgery, such as physical information of a patient and information about a surgical procedure. Further, for example, the user may input, via the input device 5047, an instruction to drive the arm unit 5031, an instruction to change imaging conditions (type of irradiation light, magnification, focal length, and the like) by the endoscope 5001, an instruction to drive the energy treatment tool 5021, or the like.

The type of the input device 5047 is not limited, and the input device 5047 may be various known input devices. As the input device 5047, for example, a mouse, a keyboard, a touch panel, a switch, a foot switch 5057, and/or a lever can be applied. When a touch panel is used as the input device 5047, the touch panel may be provided on a display surface of the display device 5041.

Alternatively, the input device 5047 is a device worn by a user such as a glasses-type wearable device or a head mounted display (HMD), and various inputs are performed in accordance with a user's gesture or gaze detected by these devices. Further, the input device 5047 includes a camera capable of detecting the movement of the user, and performs various inputs in accordance with the user's gesture or gaze detected from the video imaged by the camera. Further, the input device 5047 includes a microphone capable of collecting a user's voice, and various inputs are performed by voice via the microphone. As described above, when the input device 5047 is configured to be capable of inputting various kinds of information in a non-contact manner, in particular, a user (for example, the operator 5067) belonging to a clean area can operate a device belonging to a dirty area in a non-contact manner. In addition, since the user can operate the device without releasing the user's hand from the surgical tool that the user possesses, the convenience for the user is improved.

A treatment tool control device 5049 controls the driving of the energy treatment tool 5021 for cauterizing and incising a tissue, sealing a blood vessel, and the like. An insufflation device 5051 feeds a gas into the body cavity of the patient 5071 through the insufflation tube 5019 to inflate the body cavity for the purpose of securing the visual field by the endoscope 5001 and securing the working space of the operator. A recorder 5053 is a device capable of recording various types of information related to surgery. A printer 5055 is a device capable of printing various types of information on surgery in various formats such as text, images, and graphs.

Hereinafter, a particularly characteristic configuration of the endoscopic surgery system 5000 will be described in more detail.

(Support Arm Device)

The support arm device 5027 includes a base unit 5029 as a base and an arm unit 5031 extending from the base unit 5029. In the illustrated example, the arm unit 5031 includes a plurality of joints 5033a, 5033b, and 5033c, and a plurality of links 5035a and 5035b connected by the joint 5033b. However, in FIG. 1, the configuration of the arm unit 5031 is illustrated in a simplified manner for simplification. Actually, the shapes, numbers and arrangements of the joints 5033a to 5033c and the links 5035a and 5035b, the directions of the rotation axes of the joints 5033a to 5033c, and the like can be appropriately set so that the arm unit 5031 has a desired degree of freedom. For example, the arm unit 5031 can be preferably configured to have six or more degrees of freedom.

Accordingly, since the endoscope 5001 can be freely moved within the movable range of the arm unit 5031, the lens barrel 5003 of the endoscope 5001 can be inserted into the body cavity of the patient 5071 from a desired direction.

The joints 5033a to 5033c are provided with actuators, and the joints 5033a to 5033c are configured to be rotatable around a predetermined rotation axis by driving the actuators. The driving of the actuator is controlled by the arm control device 5045, whereby the rotation angles of the joints 5033a to 5033c are controlled, and the driving of the arm unit 5031 is controlled. Thereby, the control of the position and posture of the endoscope 5001 can be realized. At this time, the arm control device 5045 can control the driving of the arm unit 5031 by various known control methods such as force control or position control.

For example, when the operator 5067 performs an appropriate operation input via the input device 5047 (including the foot switch 5057), the driving of the arm unit 5031 may be appropriately controlled by the arm control device 5045 in accordance with the operation input, so as to control the position and posture of the endoscope 5001. With this control, after the endoscope 5001 at the tip of the arm unit 5031 is moved from an arbitrary position to an arbitrary position, the endoscope can be fixedly supported at the position after the movement. Note that the arm unit 5031 may be operated by a so-called master slave method. In this case, the arm unit 5031 can be remotely controlled by the user via the input device 5047 provided at a place away from the operating room.

When the force control is applied, the arm control device 5045 may perform so-called power assist control of driving the actuators of the joints 5033a to 5033c so that an external force is received from the user, and the arm unit 5031 moves smoothly according to the external force. Accordingly, when the user moves the arm unit 5031 while directly touching the arm unit 5031, the arm unit 5031 can be moved with a relatively light force.

Therefore, the endoscope 5001 can be moved more intuitively and with a simpler operation, and user convenience can be improved.

Here, generally, in the endoscopic surgery, the endoscope 5001 is supported by a doctor called a scopist. On the other hand, by using the support arm device 5027, the position of the endoscope 5001 can be more reliably fixed without manual operation. Thus, the image of the operation site can be stably obtained, and the surgery can be performed smoothly.

Note that the arm control device 5045 is not necessarily provided in the cart 5037. Further, the arm control device 5045 is not necessarily one device. For example, the arm control device 5045 may be provided in each of the joints 5033a to 5033c of the arm unit 5031 of the support arm device 5027, and the drive control of the arm unit 5031 may be realized when the plurality of arm control devices 5045 cooperate with each other.

(Light Source Device)

The light source device 5043 supplies the endoscope 5001 with irradiation light at the time of imaging the operation site. The light source device 5043 includes, for example, a white light source including an LED and a laser light source, or a combination thereof. At this time, when the white light source is configured by a combination of RGB laser light sources, the output intensity and output timing of each color (each wavelength) can be controlled with high precision. Thus, the white balance of the captured image can be adjusted in the light source device 5043. In this case, the laser light from each of the RGB laser light sources is emitted to the observation target in a time-division manner, and the driving of the imaging element of the camera head 5005 is controlled in synchronization with the irradiation timing, whereby the image corresponding to each of the RGB can be captured in a time-division manner. According to this method, a color image can be obtained without providing a color filter in the imaging element.

Further, the driving of the light source device 5043 may be controlled so as to change the intensity of light to be output at predetermined time intervals. When the driving of the imaging element of the camera head 5005 is controlled in synchronization with the timing of the intensity change of the light to obtain an image in a time-division manner, and the image is synthesized, it is possible to generate a so-called high dynamic range image without black spotting and white spotting.

Further, the light source device 5043 may be configured to be able to supply light in a predetermined wavelength band corresponding to special light observation. In the special light observation, for example, by utilizing the wavelength dependence of light absorption in body tissue, light is emitted in a narrow band compared to irradiation light (that is, white light) during normal observation so as to perform a so-called narrow band imaging of imaging a predetermined tissue such as a blood vessel of a mucosal surface layer with high contrast. Alternatively, in the special light observation, fluorescence observation may be performed in which an image is obtained by fluorescence generated by emitting excitation light. In the fluorescence observation, a body tissue can be irradiated with excitation light to observe fluorescence from the body tissue (autofluorescence observation), or a reagent such as indocyanine green (ICG) is locally injected into the body tissue, and the excitation light corresponding to the fluorescence wavelength of the reagent is emitted to the body tissue, so as to obtain a fluorescent image. The light source device 5043 can be configured to be able to supply narrowband light and/or excitation light corresponding to such special light observation.

(Camera Head and CCU)

Figure 2:
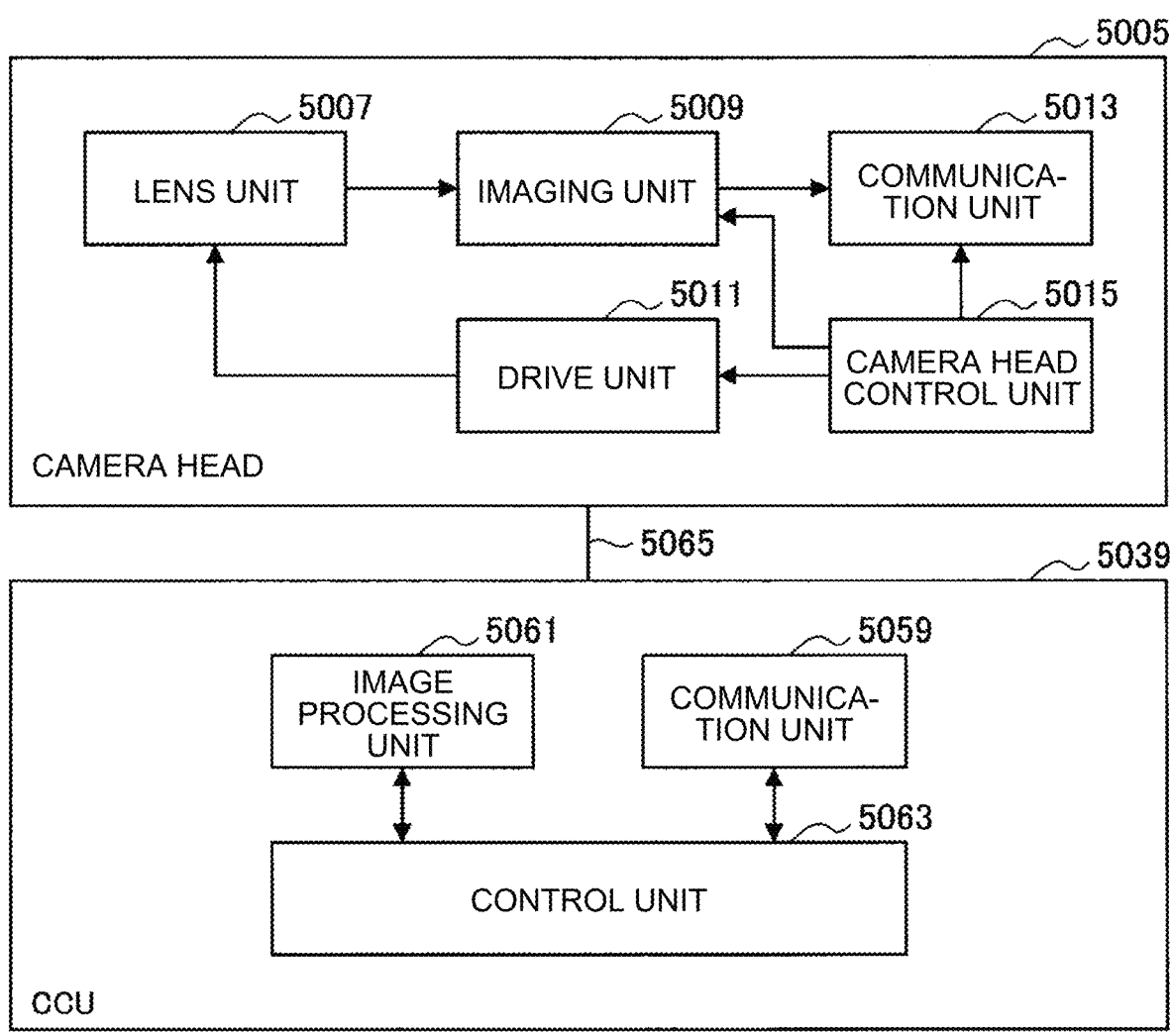
FIG. 2 is a block diagram illustrating an example of a functional configuration of a camera head and a CCU illustrated in FIG. 1.

With reference to FIG. 2, the functions of the camera head 5005 of the endoscope 5001 and the CCU 5039 will be described in more detail. FIG. 2 is a block diagram illustrating an example of a functional configuration of the camera head 5005 and the CCU 5039 illustrated in FIG. 1.

Referring to FIG. 2, the camera head 5005 includes, as the functions thereof, a lens unit 5007, an imaging unit 5009, a drive unit 5011, a communication unit 5013, and a camera head control unit 5015. Also, the CCU 5039 includes, as the functions thereof, a communication unit 5059, an image processing unit 5061, and a control unit 5063. The camera head 5005 and the CCU 5039 are communicably connected by a transmission cable 5065.

First, the functional configuration of the camera head 5005 will be described. The lens unit 5007 is an optical system provided at a connection with the lens barrel 5003. The observation light taken in from the tip of the lens barrel 5003 is guided to the camera head 5005 and enters the lens unit 5007. The lens unit 5007 is configured by combining a plurality of lenses including a zoom lens and a focus lens. The optical characteristics of the lens unit 5007 are adjusted so that the observation light is condensed on the light receiving surface of the imaging element of the imaging unit 5009. Further, the zoom lens and the focus lens are configured such that the positions thereof on the optical axis are movable for adjusting the magnification and the focus of the captured image.

The imaging unit 5009 is configured of an imaging element, and is arranged at a stage subsequent to the lens unit 5007. The observation light that has passed through the lens unit 5007 is condensed on the light receiving surface of the imaging element, and an image signal corresponding to the observation image is generated by photoelectric conversion. The image signal generated by the imaging unit 5009 is provided to the communication unit 5013.

As the imaging element that forms the imaging unit 5009, for example, a color photographable image sensor having a Bayer array is used which is complementary metal oxide semiconductor (CMOS) type. Incidentally, as the imaging element, an imaging element capable of capturing an image having a high-resolution of, for example, 4K or more may be used. When the image of the operation site is obtained with high resolution, the operator 5067 can grasp the state of the operation site in more detail, and can progress the surgery more smoothly.

In addition, the imaging element included in the imaging unit 5009 is configured to include a pair of imaging elements for obtaining right-eye and left-eye image signals corresponding to 3D display. By performing the 3D display, the operator 5067 can more accurately grasp the depth of the living tissue at the operation site. When the imaging unit 5009 is configured as a multi-plate type, a plurality of lens units 5007 are also provided corresponding to respective imaging elements.

Further, the imaging unit 5009 is not necessarily provided in the camera head 5005. For example, the imaging unit 5009 may be provided inside the lens barrel 5003 immediately after the objective lens.

The drive unit 5011 is configured by an actuator, and the zoom lens and the focus lens of the lens unit 5007 are moved by a predetermined distance along the optical axis under the control of the camera head control unit 5015. Thereby, the magnification and the focus of the image captured by the imaging unit 5009 can be appropriately adjusted.

The communication unit 5013 is configured by a communication device for transmitting and receiving various information to and from the CCU 5039. The communication unit 5013 transmits the image signal obtained from the imaging unit 5009 as RAW data to the CCU 5039 via the transmission cable 5065. At this time, it is preferable that the image signal be transmitted by optical communication in order to display the captured image of the operation site with low latency. During surgery, the operator 5067 performs the surgery while observing the state of the affected part with the captured image. Thus, for safer and more reliable surgery, the moving images of the operation site are required to be displayed in real time as much as possible. When optical communication is performed, the communication unit 5013 is provided with a photoelectric conversion module that converts an electric signal into an optical signal. The image signal is converted into an optical signal by the photoelectric conversion module, and then transmitted to the CCU 5039 via the transmission cable 5065.

Further, communication unit 5013 receives a control signal for controlling the driving of the camera head 5005 from the CCU 5039. The control signal includes information about imaging conditions such as information that specifies the frame rate of the captured image, information that specifies the exposure value at the time of imaging, and/or information that specifies the magnification and focus of the captured image. The communication unit 5013 provides the received control signal to the camera head control unit 5015. Note that the control signal from the CCU 5039 may also be transmitted by optical communication. In this case, the communication unit 5013 is provided with a photoelectric conversion module that converts an optical signal into an electric signal. The control signal is converted into an electric signal by the photoelectric conversion module and then is provided to the camera head control unit 5015.

Note that the above-described imaging conditions such as the frame rate, the exposure value, the magnification, and the focus are automatically set by the control unit 5063 of the CCU 5039 based on the obtained image signal. That is, a so-called auto exposure (AE) function, an auto focus (AF) function, and an auto white balance (AWB) function are mounted on the endoscope 5001.

The camera head control unit 5015 controls the driving of the camera head 5005 based on the control signal from the CCU 5039 received via the communication unit 5013. For example, the camera head control unit 5015 controls the driving of the imaging element of the imaging unit 5009 based on the information for specifying the frame rate of the captured image and/or the information for specifying the exposure at the time of imaging. In addition, for example, the camera head control unit 5015 appropriately moves the zoom lens and the focus lens of the lens unit 5007 via the drive unit 5011 based on information for specifying the magnification and the focus of the captured image. The camera head control unit 5015 may further include a function of storing information for identifying the lens barrel 5003 and the camera head 5005.

By arranging the lens unit 5007, the imaging unit 5009, and the like in a hermetically sealed structure having high airtightness and waterproofness, the camera head 5005 can have resistance to autoclave sterilization.

Next, the functional configuration of the CCU 5039 will be described. The communication unit 5059 is configured by a communication device for transmitting and receiving various information to and from the camera head 5005. The communication unit 5059 receives an image signal transmitted from the camera head 5005 via the transmission cable 5065. At this time, as described above, the image signal can be suitably transmitted by optical communication. In this case, in response to optical communication, the communication unit 5059 is provided with a photoelectric conversion module that converts an optical signal into an electric signal. The communication unit 5059 provides the image signal converted to the electric signal to the image processing unit 5061.

The communication unit 5059 transmits a control signal for controlling the driving of the camera head 5005 to the camera head 5005. The control signal may also be transmitted by optical communication.

The image processing unit 5061 performs various types of image processes on an image signal that is RAW data transmitted from the camera head 5005. For example, the image process includes various known signal processes such as a development process, a high image quality process (such as a band enhancement process, a super-resolution process, a noise reduction (NR) process, and/or a camera shake correction process), and/or an enlargement process (electronic zoom process). Further, the image processing unit 5061 performs a detection process on the image signal for performing AE, AF, and AWB.

The image processing unit 5061 is configured by a processor such as a CPU and a GPU, and the processor operates according to a predetermined program so as to perform the above-described image process and detection process. When the image processing unit 5061 is configured by a plurality of GPUs, the image processing unit 5061 divides information on an image signal as appropriate, and performs the image process in parallel by the plurality of GPUs.

The control unit 5063 performs various controls related to the imaging of the operation site by the endoscope 5001 and the display of the captured image. For example, the control unit 5063 generates a control signal for controlling the driving of the camera head 5005. At this time, when the imaging condition is input by the user, the control unit 5063 generates a control signal based on the input by the user. Alternatively, when the endoscope 5001 has an AE function, an AF function, and an AWB function, the control unit 5063 appropriately calculates the optimal exposure value, focal length, and white balance according to the result of the detection process by the image processing unit 5061, and generates a control signal.

Further, the control unit 5063 causes the display device 5041 to display an image of the operation site based on the image signal on which the image process is performed by the image processing unit 5061. At this time, the control unit 5063 recognizes various objects in the operative image using various image recognition techniques.

For example, the control unit 5063 detects a shape, a color, and the like of an edge of an object included in the operative image, thereby recognizing a surgical tool such as forceps, a specific living body part, bleeding, a mist at the time of using the energy treatment tool 5021, and the like. When the image of the operation site is displayed on the display device 5041, the control unit 5063 superimposes and displays various kinds of operation support information on the image of the operation site using the recognition result. When the operation support information is superimposed and displayed to be presented to the operator 5067, the surgery can be performed more safely and reliably.

The transmission cable 5065 connecting the camera head 5005 and the CCU 5039 is an electric signal cable corresponding to electric signal communication, an optical fiber corresponding to optical communication, or a composite cable thereof.

Here, in the illustrated example, the communication is performed by wire using the transmission cable 5065, but the communication between the camera head 5005 and the CCU 5039 may be performed wirelessly. When the communication between the camera head and the CCU 5039 is performed wirelessly, it is not necessary to lay the transmission cable 5065 in the operating room. Thus, a situation can be solved in which the movement of the medical staff in the operating room is hindered by the transmission cable 5065.

As above, an example of the endoscopic surgery system 5000 to which the technology according to the present disclosure can be applied has been described. Here, the endoscopic surgery system 5000 has been described as an example, but a system to which the technology according to the present disclosure can be applied is not limited to such an example. For example, the technology according to the present disclosure may be applied to an inspection flexible endoscope system or a microscopic surgery system.

<1.2. Specific Configuration Example of Medical Support Arm Device>

Next, a specific configuration example of the medical support arm device according to the embodiment of the present disclosure will be described in detail. The support arm device described below is an example configured as a support arm device that supports an endoscope at the tip of an arm unit, but this embodiment is not limited to this example.

Figure 3:
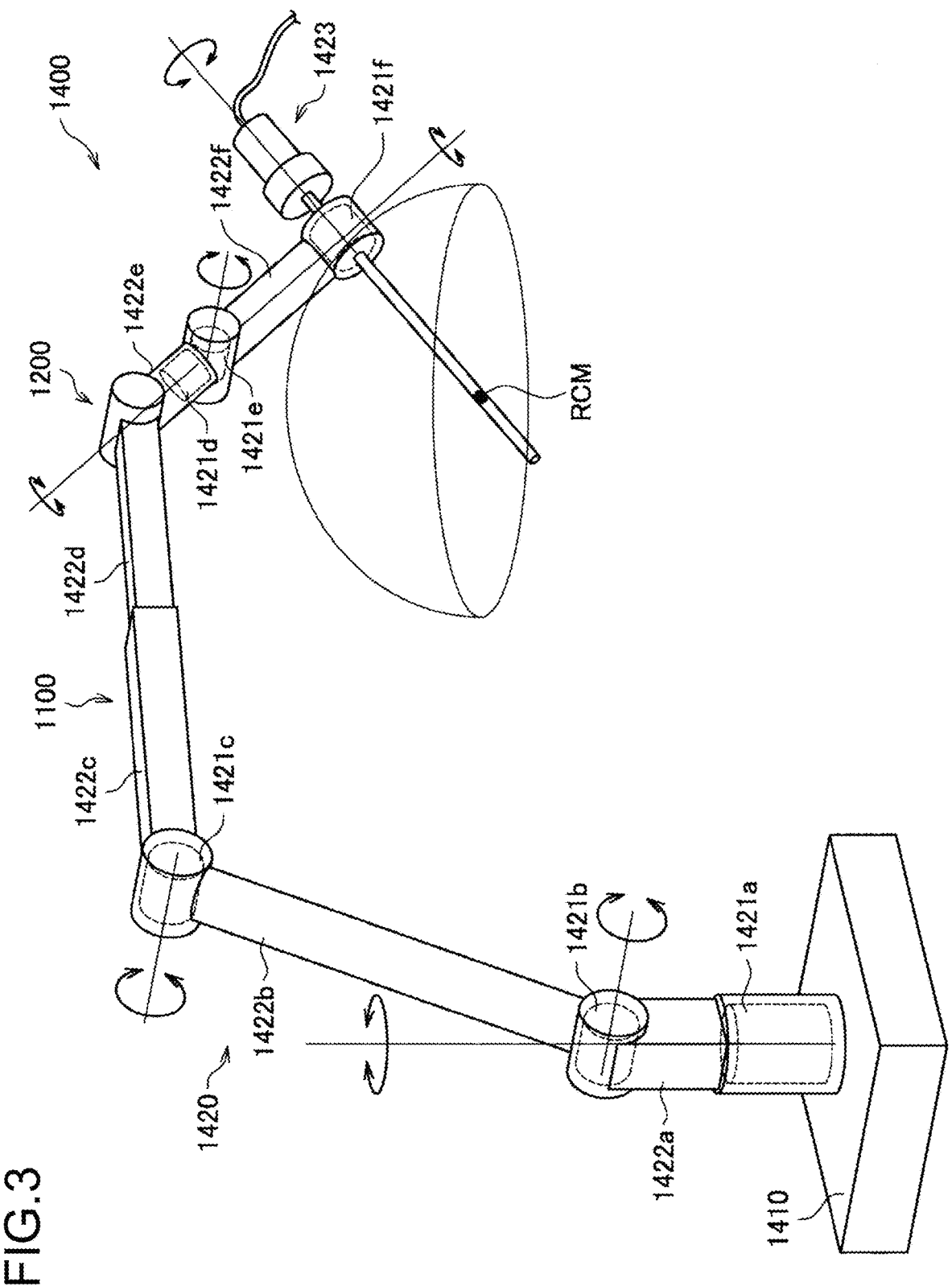
FIG. 3 is a perspective view illustrating a configuration example of a medical support arm device according to an embodiment of the present disclosure.

First, a schematic configuration of a support arm device 1400 according to this embodiment will be described with reference to FIG. 3. FIG. 3 is a schematic view illustrating an appearance of the support arm device 1400 according to this embodiment.

The support arm device 1400 according to this embodiment includes a base unit 1410 and an arm unit 1420. The base unit 1410 is a base of the support arm device 1400, and the arm unit 1420 extends from the base unit 1410. Although not illustrated in FIG. 3, a control unit that integrally controls the support arm device 1400 may be provided in the base unit 1410, and the driving of the arm unit 1420 may be controlled by the control unit. The control unit includes various signal processing circuits such as a CPU and a DSP.

The arm unit 1420 includes a plurality of active joints 1421a to 1421f, a plurality of links 1422a to 1422f, and an endoscope device 423 as a tip unit provided at the tip of the arm unit 1420.

The links 1422a to 1422f are substantially rod-shaped members. One end of the link 1422a is connected to the base unit 1410 via the active joint 1421a, the other end of the link 1422a is connected to one end of the link 1422b via the active joint 1421b, and the other end of the link 1422b is connected to one end of the link 1422c via the active joint 1421c. The other end of the link 1422c is connected to the link 1422d via a passive slide mechanism 1100, and the other end of the link 1422d is connected to one end of the link 1422e via a passive joint 200. The other end of the link 1422e is connected to one end of the link 1422f via the active joints 1421d and 1421e. The endoscope device 1423 is connected to the tip of the arm unit 1420, that is, the other end of the link 1422f via the active joint 1421f. As described above, the ends of the plurality of links 1422a to 1422f are connected to each other by the active joints 1421a to 1421f, the passive slide mechanism 1100, and the passive joint 1200 with the base unit 1410 as a fulcrum, thereby forming an arm shape extending from the base unit 1410.

The position and posture of the endoscope device 1423 are controlled by driving and controlling the actuators provided in the active joints 1421a to 1421f of the arm unit 1420. In this embodiment, the tip of the endoscope device 1423 enters the body cavity of the patient, which is the operation site, and the endoscope device captures a partial area of the operation site. However, the tip unit provided at the tip of the arm unit 1420 is not limited to the endoscope device 1423, and various medical instruments may be connected to the tip of the arm unit 1420 as a tip unit. As described above, the support arm device 1400 according to this embodiment is configured as a medical support arm device including a medical instrument.

Here, the support arm device 1400 will be described below by defining coordinate axes as illustrated in FIG. 3. Also, a vertical direction, a front-back direction, and a right-left direction are defined in accordance with the coordinate axes. That is, the vertical direction with respect to the base unit 1410 installed on the floor is defined as a z-axis direction and the vertical direction. The direction which is orthogonal to the z-axis and the direction and in which the arm unit 1420 extends from the base unit 1410 (that is, the direction in which the endoscope device 1423 is located with respect to the base unit 1410) is defined as a y-axis direction and the front-back direction. Further, directions orthogonal to the y-axis and the z-axis are defined as an x-axis direction and the right-left direction.

The active joints 1421a to 1421f connect the links with each other so as to be rotatable. Each of the active joints 1421a to 1421f has an actuator, and has a rotation mechanism that is driven to rotate about a predetermined rotation axis by driving the actuator. By controlling the rotational driving of each of the active joints 1421*a* to 1421*f*, it is possible to control the driving of the arm unit 1420, for example, extending or contracting (folding) the arm unit 1420. Here, the driving of the active joints 1421*a* to 1421*f* can be controlled by, for example, known whole-body cooperative control and ideal joint control. As described above, since the active joints 1421*a* to 1421*f* have a rotation mechanism, in the following description, the drive control of the active joints 1421*a* to 1421*f* specifically means the control of the rotation angles and/or the generated torque (the torque generated by the active joints 1421*a* to 1421*f*) of the active joints 1421*a* to 1421*f*.

The passive slide mechanism 1100 is one aspect of a passive form changing mechanism, and connects the link 1422*c* and the link 1422*d* to each other along a predetermined direction so as to be able to advance and retreat. For example, the passive slide mechanism 1100 may connect the link 1422*c* and the link 1422*d* to each other so as to be able to move directly. However, the reciprocating motion between the link 1422*c* and the link 1422*d* is not limited to a linear motion, and may be a reciprocating motion in an arc-shaped direction. For example, the passive slide mechanism 1100 is operated by a user to advance and retreat, so as to change the distance between the active joint 1421*c* at one end of the link 1422*c* and the passive joint 1200. Accordingly, the overall form of the arm unit 1420 may change. Details of the configuration of the passive slide mechanism 1100 will be described later.

The passive joint 1200 is one aspect of the passive form changing mechanism, and connects the link 1422*d* and the link 1422*e* to each other to be rotatable. For example, the passive joint 1200 is rotated by a user, so as to change the angle formed between the link 1422*d* and the link 1422*e*. Accordingly, the overall form of the arm unit 1420 may change. Details of the configuration of the passive joint 1200 will be described later.

In this specification, the "posture of the arm unit" means the state of the arm unit which can be changed by the drive control of the actuators provided in the active joints 1421*a* to 1421*f* by the control unit in a state where the distance between the active joints adjacent to each other across one or more links is constant. The "form of the arm" means the state of the arm unit that can be changed by changing the distance between the active joints adjacent to each other across the link or the angle between the links connecting the adjacent active joints according to the operation of the passive form changing mechanism.

The support arm device 1400 according to this embodiment includes six active joints 1421*a* to 1421*f*, and has six degrees of freedom in driving the arm unit 1420. That is, the drive control of the support arm device 1400 is realized by the drive control of the six active joints 1421*a* to 1421*f* by the control unit, while the passive slide mechanism 1100 and the passive joint 1200 is not subject to the drive control by the control unit.

Specifically, as illustrated in FIG. 3, the active joints 1421*a*, 1421*d*, and 1421*f* are provided such that the long axis direction of each of the connected links 1422*a* and 1422*e* and the imaging direction of the connected endoscope device 1423 are set as rotation axis directions. The active joints 1421*b*, 1421*c*, and 1421*e* are provided such that the x-axis direction in which the connection angle of each of the connected links 1422*a* to 1422*c*, 1422*e*, and 1422*f* and the endoscope device 423 is changed in a y-z plane (a plane defined by the y axis and the z axis) is set as the rotation axis direction. As described above, in this embodiment, the active joints 1421*a*, 1421*d*, and 1421*f* have a function of performing so-called yawing, and the active joints 1421*b*, 1421*c*, and 1421*e* have a function of performing so-called pitching.

With such a configuration of the arm unit 1420, the support arm device 1400 according to this embodiment has six degrees of freedom in driving the arm unit 1420. Thus, the endoscope device 1423 can be freely moved within the movable range of the arm unit 1420. FIG. 3 illustrates a hemisphere as an example of a movable range of the endoscope device 1423. If the center point RCM (remote movement center) of the hemisphere is the imaging center of the operation site to be imaged by the endoscope device 1423, when the endoscope device 1423 is moved on the spherical surface of the hemisphere with the imaging center of the endoscope device 1423 fixed at the center point of the hemisphere, the operation site can be photographed from various angles.

Further, the arm unit 1420 may have a degree of freedom of 1421*g* for rotating the endoscope device 1423 coaxially with the link 1422*f*, in addition to the degree of freedom described above. Accordingly, the endoscope device 1423 can be rotated with the longitudinal axis of the link 1422*f* as the rotation axis.

<1.3. Configuration Example of Control Device>>

So far, the configuration of the support arm device 1400 according to this embodiment has been described. Hereinafter, a configuration example of the control device for the drive control of the arm unit 1420 in the support arm device 1400 according to this embodiment, that is, for controlling the rotational driving of the actuators 1430 provided in the active joints 1421*a* to 1421*f* will be described.

Figure 4:
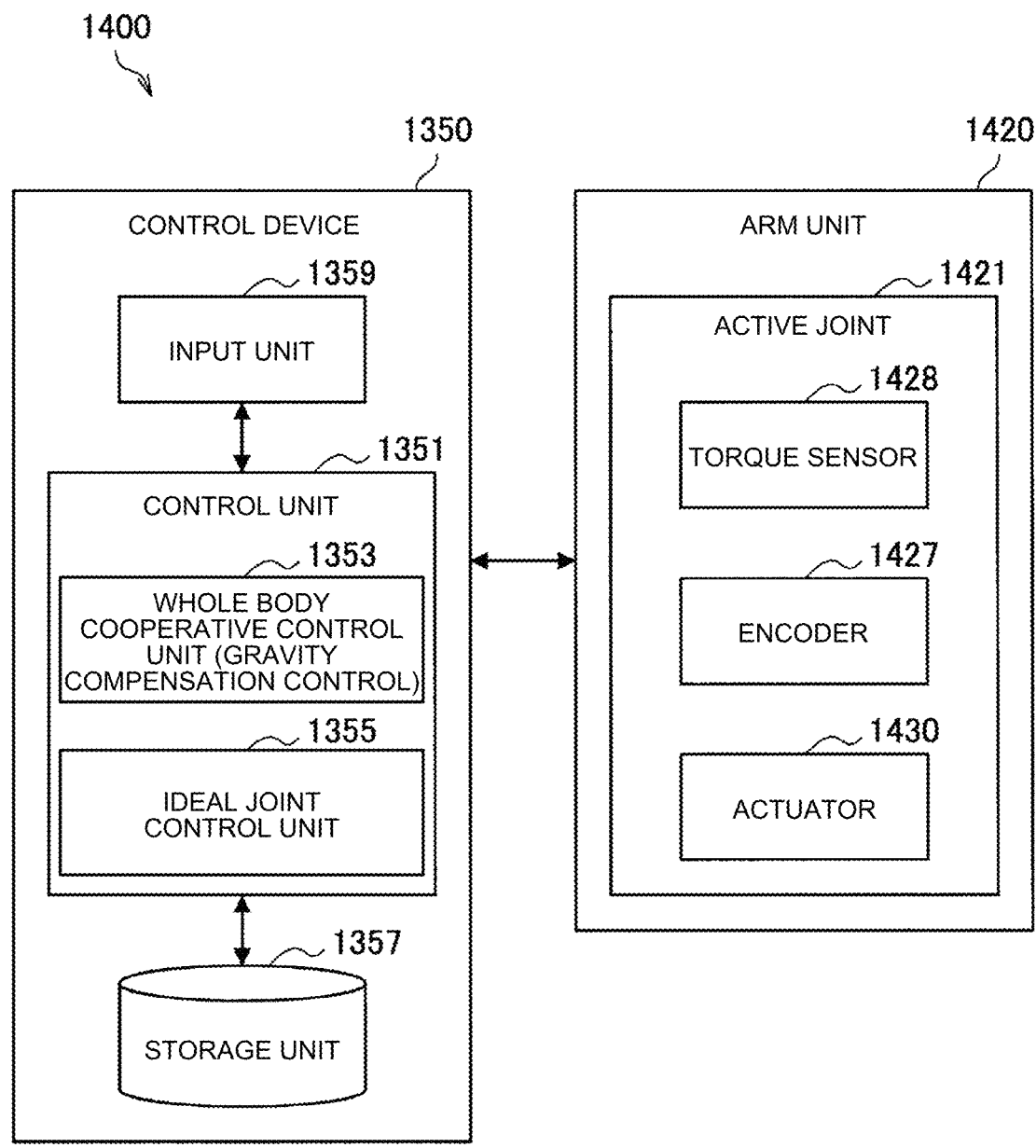
FIG. 4 is a block diagram illustrating a configuration example of a medical support arm device.

FIG. 4 is a block diagram illustrating an overall configuration example of the support arm device 1400 including a control device 1350. The control device 1350 includes a control unit 1351, a storage unit 1357, and an input unit 1359.

The control unit 1351 is configured by various signal processing circuits such as a CPU and a DSP. The control unit 1351 integrally controls the control device 1350 and performs various calculations for controlling the driving of the arm unit 1420 in the support arm device 1400. Specifically, the control unit 1351 has a whole-body cooperative control unit 1353 and an ideal joint control unit 1355. The whole-body cooperative control unit 1353 performs various calculations in whole-body cooperative control in order to drive and control actuators 1430 provided in the active joints 1421*a* to 1421*f* of the arm unit 1420 of the support arm device 1400. The ideal joint control unit 1355 performs various calculations in the ideal joint control that realizes an ideal response to the whole-body cooperative control by correcting the influence of disturbance. The storage unit 1357 may be a storage element such as a Random Access Memory (RAM) or a Read Only Memory (ROM), or may be a semiconductor memory, a hard disk, or an external storage device.

The input unit 359 is an input interface for the user to input information, instructions, and the like regarding drive control of the support arm device 400 to the control unit 351. The input unit 359 has an operating unit, which is operated by a user, such as a lever and a pedal, and according to the operation of the lever, pedal, or the like, the position, speed, or the like of each component of the arm unit 420 may be set for an instantaneous exercise purpose. In addition to the lever and the pedal, the input unit 359 may include, for example, an operation unit, which is operated by a user, such as a mouse, a keyboard, a touch panel, a button, and a switch.

The arm unit 1420 controlled by the control device 1350 includes an active joint 1421. The active joints 1421 (1421*a* to 1421*f*) includes various components necessary for driving the arm unit 1420, such as a support member for connecting or supporting the links 1422*a* to 1422*f* and the endoscope device 1423. In the above description and the following description, the driving of the joint of the arm unit 1420 may mean the driving of the actuator 430 in the active joints 1421*a* to 1421*f*.

The active joint 1421 includes a torque sensor 1428, an encoder 1427, and an actuator 1430. In FIG. 4, the actuator 1430, the encoder 1427, and the torque sensor 1428 are illustrated separately, but the encoder 1427 and the torque sensor 1428 may be included in the actuator 1430.

The actuator 1430 includes a motor, a motor driver, and a speed reducer. The actuator 1430 is, for example, an actuator corresponding to force control. In the actuator 1430, the rotation of the motor is reduced at a predetermined reduction ratio by the speed reducer to be transmitted to another member at the subsequent stage via the output shaft, thereby driving the other member.

The motor is a driving mechanism that generates a rotational driving force. The motor is driven so as to generate a torque corresponding to a torque command value from the control unit under the control of the motor driver. As the motor, for example, a brushless motor is used. However, this embodiment is not limited to this example, and various known types of motors may be used as the motor.

A motor driver is a driver circuit (driver IC (Integrated Circuit)) that drives the motor to rotate by supplying current to the motor. The motor driver can control the number of rotations of the motor by adjusting the amount of current supplied to the motor. The motor driver drives the motor by supplying a current corresponding to the torque command value τ from the control unit to the motor.

In addition, the motor driver can adjust the amount of current supplied to the motor to adjust the coefficient of viscous resistance in the rotational movement of the actuator 1430. As a result, a predetermined resistance can be applied to the rotational movement of the actuator 1430, that is, the rotational movement of the active joints 1421*a* to 1421*f*. For example, the active joints 1421*a* to 1421*f* can be set in a state where the active joints are easy to be rotated by an externally applied force (that is, a state where the arm unit 1420 is easy to be moved manually) and, conversely, also can be set in a state where the active joints are hard to be rotated by an externally applied force (that is, a state where the arm unit 1420 is hard to be moved manually).

A speed reducer is connected to a rotation shaft (drive shaft) of the motor. The speed reducer reduces the rotation speed (that is, the rotation speed of the input shaft) of the connected rotation shaft of the motor at a predetermined reduction ratio and transmits the reduced speed to the output shaft. In this embodiment, the configuration of the speed reducer is not limited to a specific one, and various known types of speed reducers may be used as the speed reducer. However, as the speed reducer, it is preferable to use a speed reducer such as Harmonic Drive (registered trademark) in which the speed reduction ratio can be set with high accuracy. Further, the speed reduction ratio of the speed reducer can be appropriately set according to the use of the actuator 1430. For example, when the actuator 1430 is applied to the active joints 1421*a* to 1421*f* of the support arm device 400 as in this embodiment, the speed reducer having a speed reduction ratio of about 1:100 can be suitably used.

The encoder 1427 detects the rotation angle of the input shaft (that is, the rotation angle of the rotation shaft of the motor). Based on the rotation speed of the input shaft detected by the encoder 1427 and the reduction ratio of the speed reducer, it is possible to obtain information such as the rotation angles, the rotation angular velocities, and the rotation angular accelerations of the active joints 1421*a* to 1421*f*. As the encoder 1427, various known rotary encoders such as a magnetic encoder and an optical encoder may be used. Note that the encoder 1427 may be provided only on the input shaft of the actuator 1430, or an encoder for detecting the rotation angle or the like of the output shaft of the actuator 1430 may be further provided at a stage subsequent to the speed reducer.

The torque sensor 1428 is connected to the output shaft of the actuator 1430, and detects the torque acting on the actuator 1430. The torque sensor 1428 detects the torque (generated torque) output by actuator 1430. The torque sensor 1428 can also detect an external torque applied to the actuator 1430 from the outside.

The configuration of the active joint 1421 has been described above. Here, in this embodiment, the operation of the arm unit 1420 is controlled by force control. In the force control, in the support arm device 1400, the rotation angle of each of the active joints 1421*a* to 1421*f* and the torque acting on each of the active joints 1421*a* to 1421*f* are detected by the encoder 1427 and the torque sensor 1428 provided for each actuator 1430, respectively. At this time, the torque acting on each of the active joints 1421*a* to 1421*f* detected by the torque sensor 1428 may include the force acting on the arm unit 1420 and/or the endoscope device 1423.

Further, based on the rotation angle detected by the encoder 1427 and the torque value detected by the torque sensor 1428, the current state (a position, a speed, and the like) of the arm unit 1420 can be obtained. In the support arm device 1400, the torque which is necessary for the arm unit 1420 to execute a desired exercise purpose and is generated by the actuator 1430 provided in each of the active joints 1421*a* to 1421*f* is calculated based on the acquired state (arm state) of the arm unit 1420, and the actuator 1430 of each of the active joints 1421*a* to 1421*f* is driven using the torque as a control value.

As the actuator 1430, various known actuators can be used which are used in various devices of which the operation is generally controlled by force control. For example, as the actuator 1430, the actuators described in JP 2009-269102 A and JP 2011-209099 A, which are prior patent applications by the present applicant, can be preferably used.

In the support arm device 1400 according to this embodiment, the configuration of the actuator 1430 and each component configuring the actuator is not limited to the above configuration, and may be another configuration.

The basic configuration of the endoscope system has been described above. Hereinafter, a specific embodiment of the above-described endoscope system will be described.

<<2. Oblique-Viewing Rotation Operation and Follow-Up Operation to Observation Target by Oblique-Viewing Endoscope>>

<2.1. Rotation Operation of Oblique-Viewing Endoscope>

Figure 5:
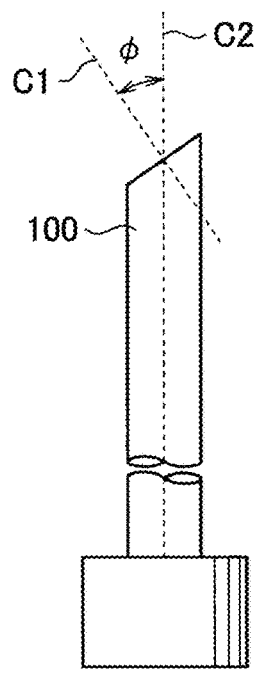
FIG. 5 is a schematic view illustrating an appearance of an oblique-viewing endoscope 100.

In this embodiment, an oblique-viewing endoscope is used as the endoscope 5001 (endoscope device 423) described above. FIG. 5 is a schematic view illustrating the appearance of the oblique-viewing endoscope 100. In the oblique-viewing endoscope 100, the direction (C1) of the objective lens toward the subject has a predetermined angle ϕ with respect to the longitudinal direction (scope axis C2)

of the oblique-viewing endoscope 100. That is, in the oblique-viewing endoscope 100, the objective optical system forms an angle with the eyepiece optical system of the scope. In the oblique-viewing endoscope 100, an operation of rotating the oblique-viewing endoscope 100 with the scope axis C2 as a rotation axis (hereinafter, referred to as oblique-viewing rotation) is performed for observation. By performing the oblique-viewing rotation, it is possible to obtain a roundabout visual field and upper, lower, right, and left peripheral visual fields.

Figure 6:
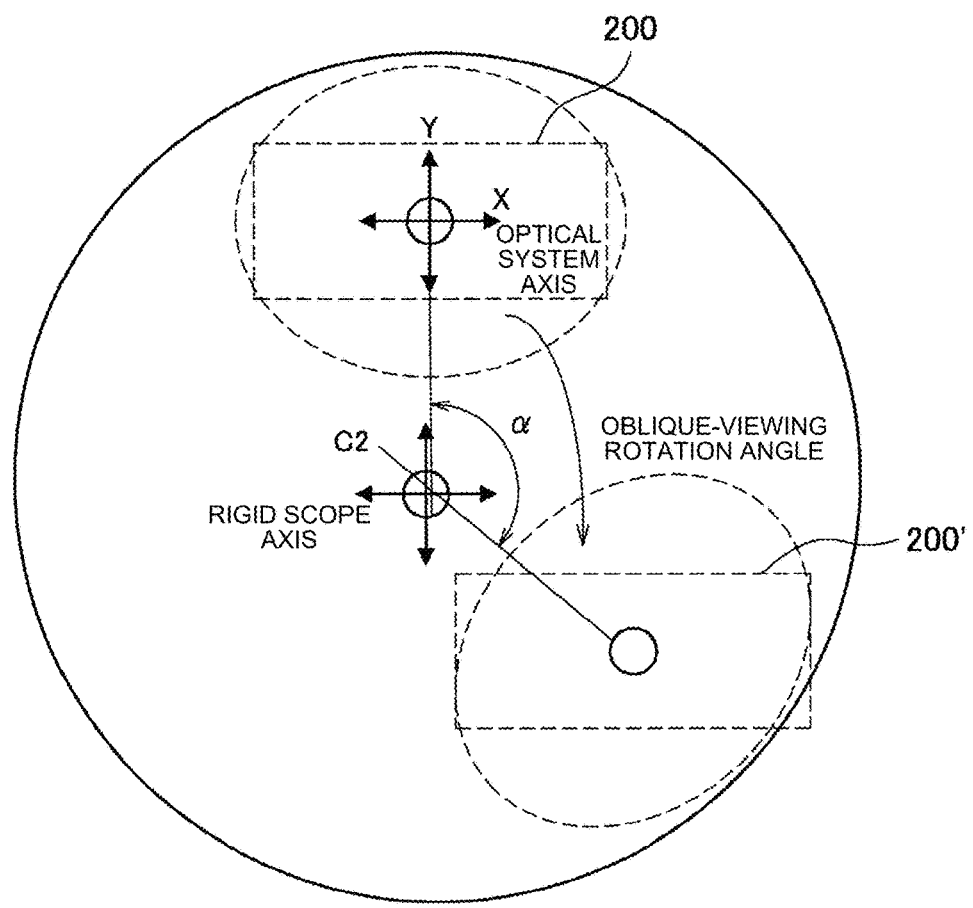
FIG. 6 is a schematic view illustrating a state in which a visual field 200 is changed by oblique-viewing rotation.

FIG. 6 is a schematic view illustrating a state in which the visual field 200 displayed on the display device 5041 is changed by the oblique-viewing rotation. As illustrated in FIG. 6, in a state in which the visual field 200 is displayed on the monitor, when the oblique-viewing endoscope is oblique-viewing-rotated by the oblique-viewing rotation angle α to control the vertical direction of the visual field 200, the visual field displayed on the monitor changes from the visual field 200 to the visual field 200'. Therefore, by controlling the two axes of the oblique-viewing rotation and the vertical direction of the camera, it is possible to obtain the upper, lower, right, and left peripheral visual fields.

Figure 7:
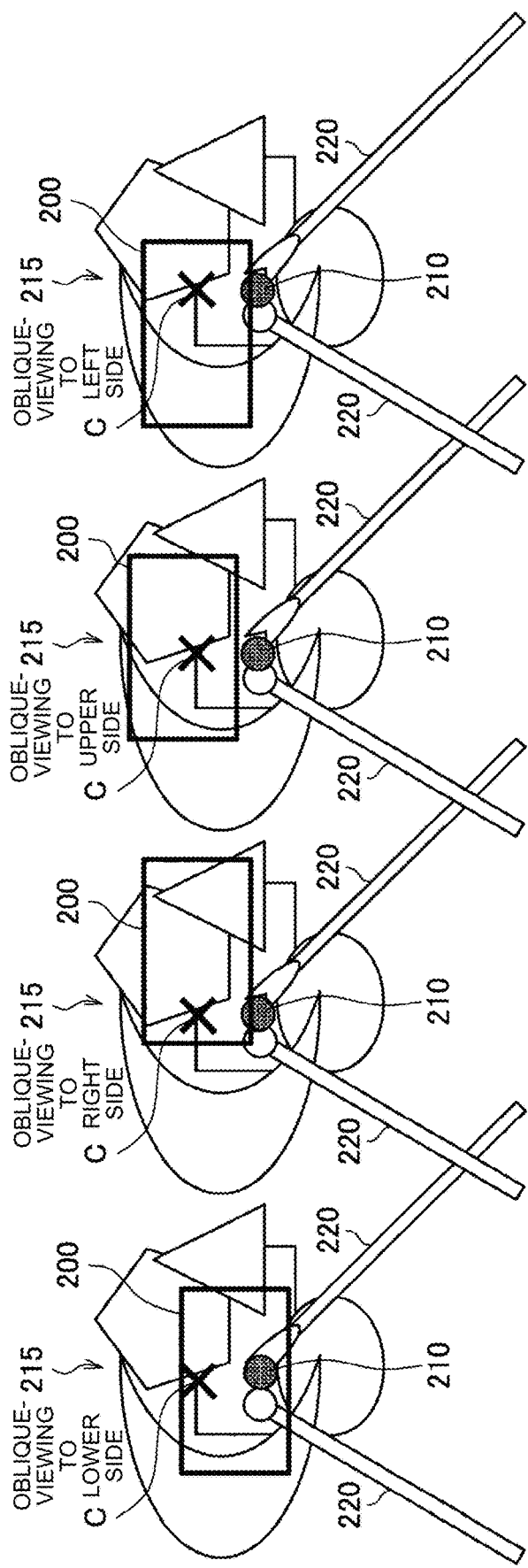
FIG. 7 is a schematic view illustrating a state in which a visual field projected on a monitor changes due to an oblique-viewing rotation.

FIG. 7 is a schematic view illustrating a state in which a visual field projected on a monitor changes due to the oblique-viewing rotation. FIG. 7 illustrates a state of observing the inside of the body with an oblique-viewing endoscope, and illustrates a state in which an observation target 210 to be viewed by a user (operator) exists in various organs 215. In FIG. 7, the visual field 200 of the monitor is illustrated in a rectangular area, and the observation target 210 and the scope axis C2 that the user (operator) wants to see are illustrated together with the visual field 200. Further, FIG. 7 illustrates a state in which the operator makes a surgical tool 220 such as forceps contact the observation target 210 and grips the observation target 210.

As illustrated in FIG. 7, the observation target 210 is located below the visual field 200 (on the side of the operator who operates the surgical tool 220) with respect to the position of the scope axis C2. FIG. 7 illustrates a state in which the observation target 210 moves with respect to the visual field 200 when the oblique-viewing endoscope 100 is rotated about the scope axis C2.

The drawing of "oblique-viewing to lower side" illustrated in FIG. 7 illustrates a state where the optical axis of the objective optical system of the oblique-viewing endoscope 100 is directed to the lower side in the vertical direction of the visual field 200. In this case, the observation target 210 enters the visual field 200, and the operator can visually recognize the observation target 210 on the monitor.

The drawing of "oblique-viewing to right side" illustrated in FIG. 7 illustrates a state where the optical axis of the objective optical system of the oblique-viewing endoscope 100 is directed to the right side in the right-left direction of the visual field 200. In this case, the observation target 210 is removed from the visual field 200, and the operator cannot visually recognize the observation target 210 on the monitor.

The drawing of "oblique-viewing to upper side" illustrated in FIG. 7 illustrates a state where the optical axis of the objective optical system of the oblique-viewing endoscope 100 is directed to the upper side in the vertical direction of the visual field 200. Further, the drawing of "oblique-viewing to left side" illustrated in FIG. 7 illustrates a state where the optical axis of the objective optical system of the oblique-viewing endoscope 100 is directed to the left side in the right-left direction of the visual field 200. Also in these cases, the observation target 210 is removed from the visual field 200, and the operator cannot visually recognize the observation target 210 on the monitor.

As described above, in the oblique-viewing endoscope 100, by performing the oblique-viewing rotation, the position of the visual field with respect to the observation target 210 can be changed, and a relatively wide range around the scope axis C2 can be visually recognized. On the other hand, as illustrated in FIG. 7, there is a possibility that a part that the user wants to see or an instrument may be out of the visual field 200 of the monitor due to the oblique-viewing rotation, so that the sight of those places may be lost.

Therefore, in this embodiment, the position of the observation target 210 is detected, and the arm is controlled so that the observation target 210 moves to the screen center. In this embodiment, the rotation speed during the oblique-viewing rotation is changed according to the position of the observation target 210 with respect to the visual field 200. Specifically, the control is performed such that the rotation speed in the oblique-viewing rotation is lower as the observation target 210 is further away from the center of the visual field 200. As the observation target 210 is further away from the center of the visual field 200, the observation target 210 deviates more easily from the visual field 200 when performing the oblique-viewing rotation. For this reason, as the observation target 210 is further away from the center of the visual field 200, the rotation speed during the oblique-viewing rotation is lower. Thus, the observation target 210 is less likely to deviate from the visual field 200, so as to suppress that the position of the observation target 210 is lost. However, the following function and the speed of the oblique-viewing rotation are different. Thus, when the moving speed having the degree of freedom to move the screen in the up, down, left and right directions for the following and the speed of the oblique-viewing rotation are not coordinated and controlled, the observation target may be off the screen. For this reason, while the observation target 210 is controlled to be at the screen center, the control is performed such that the speed of the oblique-viewing rotation is reduced according to the distance L from the screen center to the target 21 or the relative position.

<2.2. Change of Oblique-Viewing Rotation Speed According to Distance from Center of the Visual Field>

Figure 8:
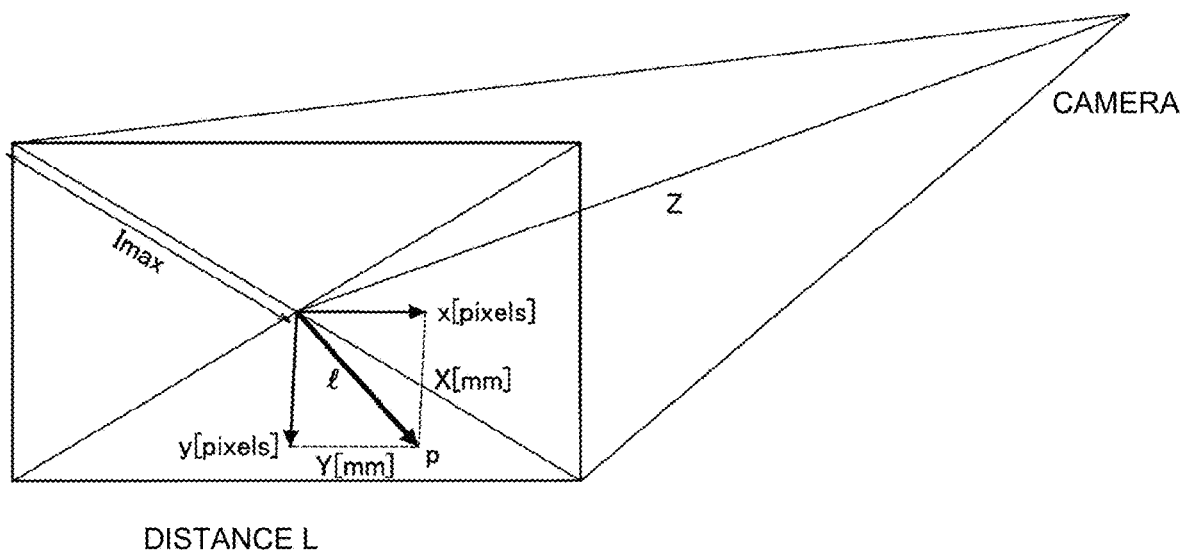
FIG. 8 is a schematic view illustrating a method for calculating a distance from the center of the visual field 200 to an observation target 210.

Here, the change of the oblique-viewing rotation speed according to the distance from the center of the visual field 200 to the observation target 210 will be described. FIG. 8 is a schematic view illustrating a method for calculating the distance from the center of the visual field 200 to the observation target 210. As illustrated in FIG. 8, when the oblique-viewing rotation speed is ω [rad/s] and the number of pixels from the screen center O to the position p of the observation target 210 is (x, y) [pixels], the number of pixels l from the screen center to the position of the observation target 210 is obtained by $l=\sqrt{(x^2+y^2)}$. From here, it is realized by adjusting with the function of the oblique-viewing rotation speed ω=f(l). For example, when the number of pixels from the screen center to the diagonal screen vertex is lmax [pixels], and the highest speed of the oblique-viewing rotation speed is ωmax, it is satisfied that ω=ωmax*(lmax−l)=ωmax*(lmax−√(x2+y2)).

Thus, the adjustment is performed in the form of ω=ωmax when the position of the observation target 210 is at the screen center, and ω=0 when the position of the observation target 210 is at the diagonal screen vertex. In this example, the calculation is linear, but a higher-order function or the like may be used. If the distance Z [mm] from the camera to the subject and the angle of view θ are known, the distance L [mm] from the screen center to the observation target 210 may be calculated to set ω=f(L).

Figure 9:
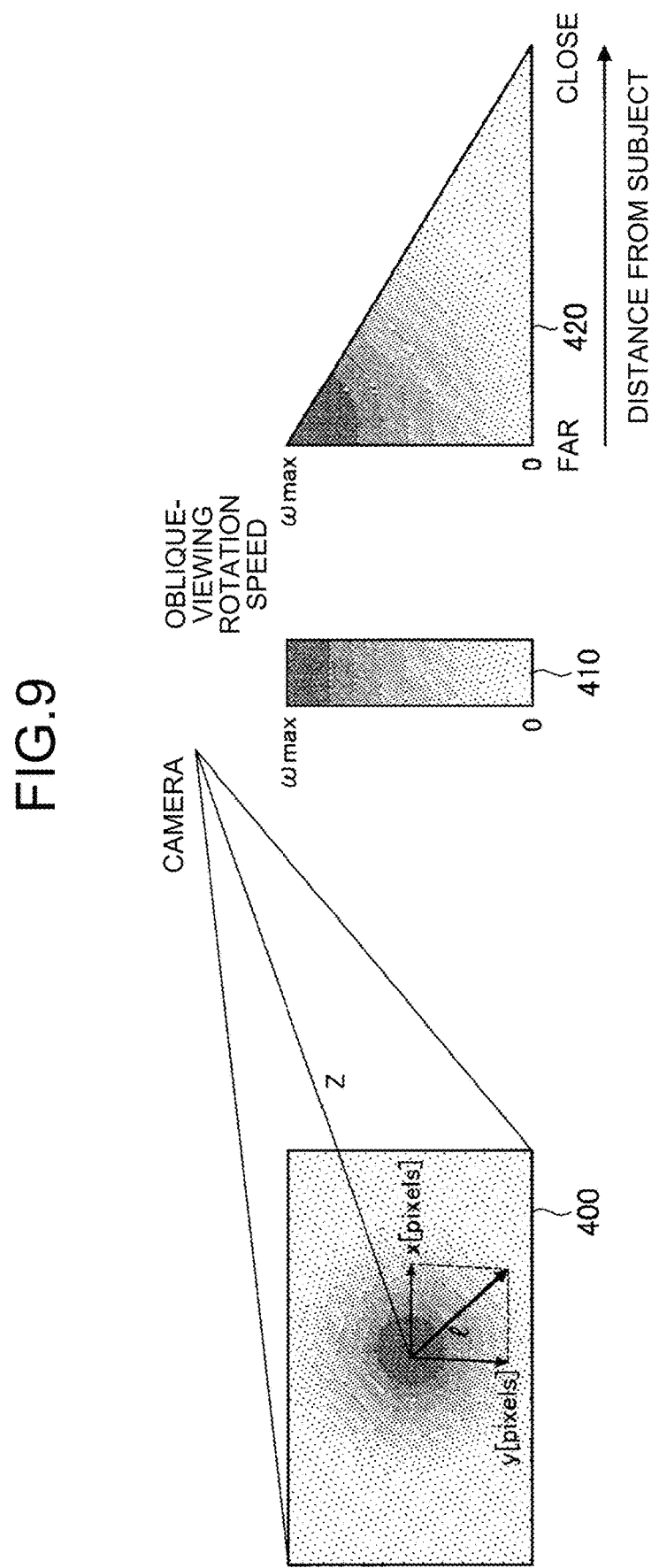
FIG. 9 is a schematic view illustrating an example of a map that defines a speed of oblique-viewing rotation according to the position of a subject in a screen.

FIG. 9 is a schematic view illustrating an example of a map that defines a speed of the oblique-viewing rotation according to the position of the subject in the screen. A map 400 shows an example based on FIG. 8 in which the speed of the oblique-viewing rotation decreases as the distance from the screen center O increases. The density of the dots in the map 400 corresponds to the speed of the oblique-viewing rotation, and the map 410 shows the relationship between the density of the dots in the map 400 and the speed of the oblique-viewing rotation. As shown in the map 410, the higher the dot density, the higher the speed of the oblique-viewing rotation. Therefore, in the map 400, the speed of the oblique-viewing rotation decreases as the distance from the screen center O increases.

The relationship between the dot density, and the speed of the oblique-viewing rotation and the distance to the subject (the observation target 210) is also shown. According to the map 420, the shorter the distance to the subject, the lower the speed of the oblique-viewing rotation. As the distance to the subject is shorter, the amount of movement of the observation target 210 in the visual field 200 in response to the movement of the oblique-viewing endoscope 100 is greater. Thus, by decreasing the speed of the oblique-viewing rotation as the distance to the subject is shorter, it is possible to prevent the sight of the observation target 210 from being lost from the visual field 200.

Figure 10:
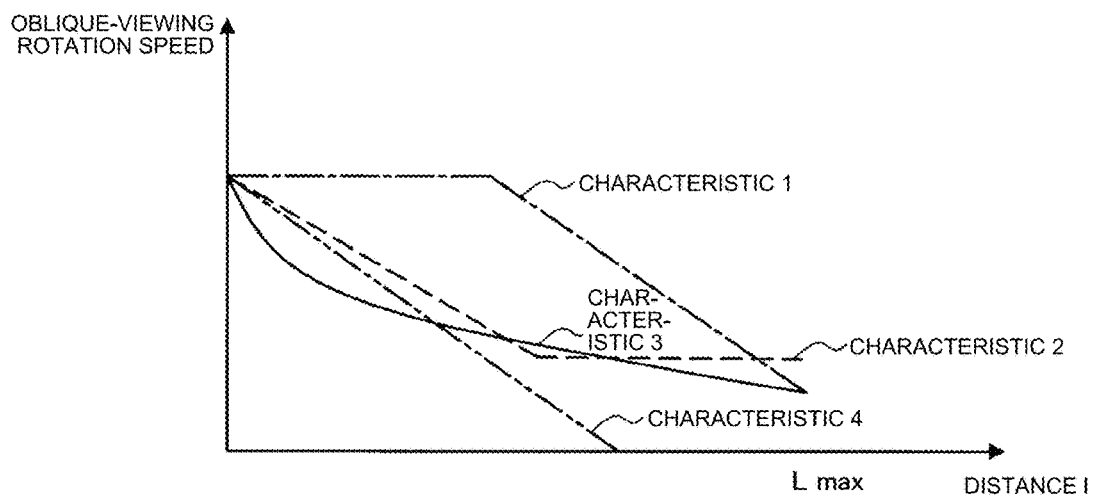
FIG. 10 is a characteristic diagram illustrating a relationship between a distance (horizontal axis) from a screen center O to the observation target 210 and an oblique-viewing rotation speed (vertical axis).

FIG. 10 is a characteristic diagram illustrating the relationship between the distance (horizontal axis) from the screen center O to the observation target 210 and the oblique-viewing rotation speed (vertical axis). As described above, the control is performed such that the speed of the oblique-viewing rotation decreases as the distance from the screen center O to the observation target 210 increases, but a variation illustrated in FIG. 10 can be assumed as a control method.

In the case of a characteristic 1 illustrated in FIG. 10, the control is performed with priority given to the speed of the oblique-viewing rotation. If the movement of the arm in the XY direction is sufficiently fast, it is possible to follow the observation target 210 even with such characteristics. Since the rotation speed of the oblique-viewing endoscope is not 0 even at the screen end (Lmax), the observation target 210 may be off the screen depending on the position of the observation target 210 at the start of the oblique-viewing rotation.

In the case of characteristics 2 and 3 illustrated in FIG. 10, a case where the speed of an XY movement of the arm is lower than the development of the visual field by the oblique-viewing rotation is assumed. When the observation target 210 is close to the screen center O, the oblique-viewing rotation is performed quickly, and the rotation speed of the oblique-viewing endoscope is not 0 even at the screen end (Lmax). Since the observation target 210 has a speed even when the observation target 210 is separated from the screen center O by a certain distance or more, the observation target 210 may be off the screen depending on the position of the observation target 210 at the start of the oblique-viewing rotation.

Further, in the case of a characteristic 4 illustrated in FIG. 10, a case where the XY movement is considerably slow and the observation target 210 is not deviated from the visual field 200 is assumed. When the observation target 210 deviates to some extent from the screen center O, the oblique-viewing rotation is completely stopped, and only the XY movement is performed.

In any of the characteristics 1 to 4, the characteristics change depending on the relationship between the maximum speed of the oblique-viewing rotation and the speed of the XY movement of the arm, whether or not the observation target 210 is allowed to move out of the visual field 200, and the like.

<2.3. Follow-Up Operation to Observation Target>

[How to Move Arm to Move Observation Target to Screen Center]

Figure 11:
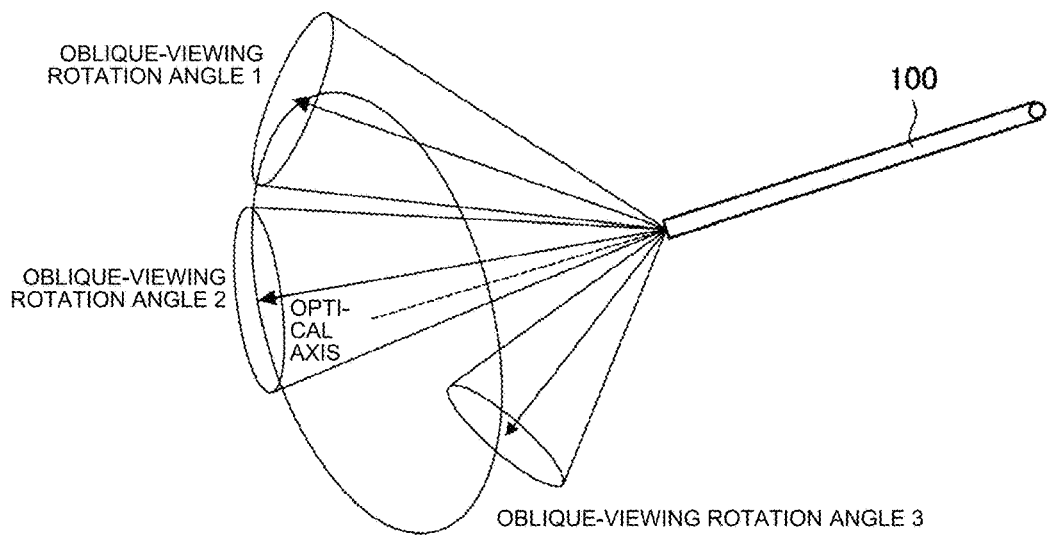
FIG. 11 is a schematic view illustrating a state in which the direction of the optical axis of the objective optical system changes due to the oblique-viewing rotation of the oblique-viewing endoscope 100.
Figure 12:
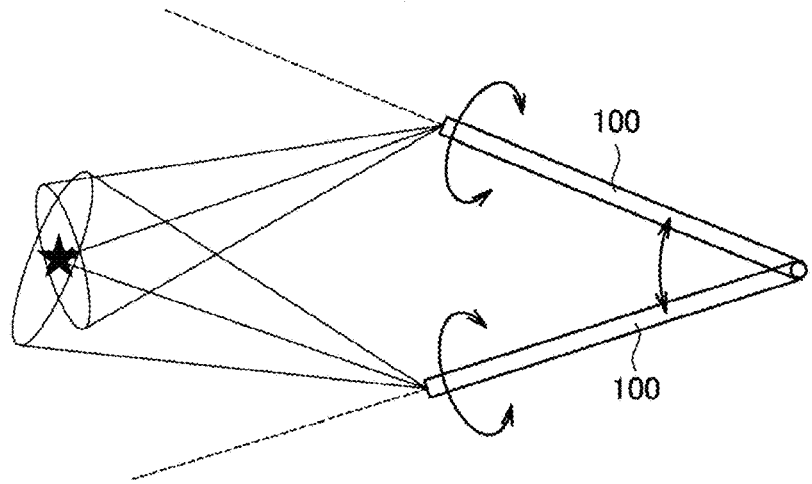
FIG. 12 is a schematic view illustrating a case where movement in an XY direction is performed by giving a rotation of the optical axis at the center of a trocar point or movement close thereto.

FIG. 11 illustrates an aspect in which the direction of the optical axis of the objective optical system changes due to the rotation (oblique-viewing rotation) of the oblique-viewing endoscope 100 around the long axis. As illustrated in FIG. 10, it is possible to change the viewing direction of the operator by the oblique-viewing rotation, but the visual field also moves as described in FIG. 7. On the other hand, FIG. 12 illustrates a case in which the movement in the XY direction is performed by giving the rotation of the optical axis at the center of the trocar point or a movement close thereto. The trocar point means a position where the trocar is inserted into a human body. As illustrated in FIG. 12, when a rotational movement (the movement of the oblique-viewing endoscope pivot) is applied to the oblique-viewing endoscope 100 about the trocar point, the oblique-viewing rotation angle can be changed without the deviation from the visual field. When performing such a movement, the oblique-viewing rotation angle and the XY movement are linked to move.

Figure 13:
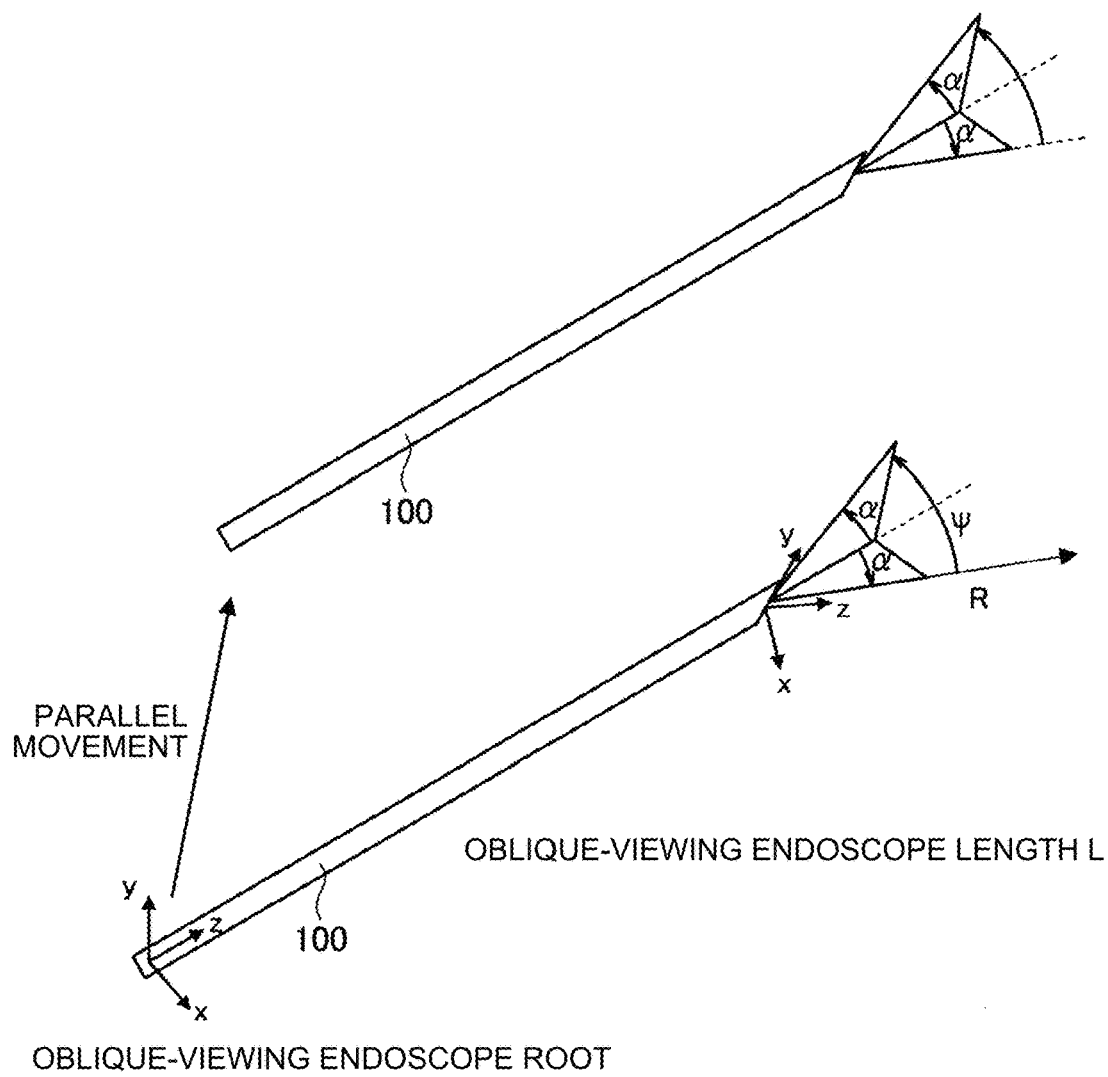
FIG. 13 illustrates an example of movement in a Y direction, and is a schematic view illustrating a case where an oblique-viewing rotation is performed together with the movement in the Y direction.

Hereinafter, an example of the method of moving the oblique-viewing endoscope 100 with respect to the visual field in combination with the oblique-viewing rotation of the oblique-viewing endoscope 100 will be described. FIG. 13 illustrates an example of parallel movement without changing the posture of the oblique-viewing endoscope, and is a schematic view illustrating a case where the oblique-viewing rotation is performed together with the parallel movement. In this case, the movement is performed without changing the posture of the oblique-viewing endoscope 100 with respect to the camera visual field.

When an oblique-viewing angle α (around the Y axis), an oblique-viewing rotation angle ψ (around the Z axis), a rigid scope length L, a distance R to the observation target, a point V at the center of the visual field, and the amount (ax, ay, az) of the parallel movement are set, the simultaneous conversion matrix representing the parallel movement is as follows.

$$T\_xyz = \begin{bmatrix} 1 & 0 & 1 & ax \\ 0 & 1 & 0 & ay \\ 0 & 0 & 1 & az \\ 0 & 0 & 0 & 1 \end{bmatrix}$$

$$Ry(\alpha) = \begin{bmatrix} \cos\alpha & 0 & \sin\alpha \\ 0 & 1 & 0 \\ -\sin\alpha & 0 & \cos\alpha \end{bmatrix}$$

$$Rz(\phi) = \begin{bmatrix} \cos\phi & -\sin\phi & 0 \\ \sin\phi & \cos\phi & 0 \\ 0 & 0 & 1 \end{bmatrix}$$

Further, the simultaneous conversion matrix of the oblique-viewing angle and the oblique-viewing rotation angle can be expressed as follows. Note that the initial position of the root of the rigid scope is set as the origin of (0, 0, 0) for simplicity.

$$T\_o = \begin{bmatrix} & & & 0 \\ & [Rz(\phi) * Ry(\alpha)] & & 0 \\ & & & L \\ 0 & 0 & 0 & 1 \end{bmatrix}$$

At this time, the point V at the center of the visual field is as follows.

$$V = T\_xyz * T\_o * \begin{bmatrix} 0 \\ 0 \\ R \\ 1 \end{bmatrix} = \begin{bmatrix} R\cos\phi\sin\alpha + ax \\ R\sin\phi\sin\alpha + ay \\ R\cos\alpha + L + az \end{bmatrix}$$

Further, the simultaneous conversion matrix of the rotation about the constraint point 300 is as follows.

$$R\_troc = \begin{bmatrix} & & & 0 \\ & [Ry(\theta) * Rx(\phi)] & & 0 \\ & & & 0 \\ 0 & 0 & 0 & 1 \end{bmatrix}$$

At this time, the point V at the center of the visual field can be expressed as follows.

$$V = T\_troc * T\_o * \begin{bmatrix} 0 \\ 0 \\ R \\ 1 \end{bmatrix} = \begin{bmatrix} R\cos\theta\cos\phi\sin\alpha + R\sin\theta\sin\phi\sin\phi\sin\alpha + R\sin\theta\cos\phi\cos\alpha + L\sin\theta\cos\phi \\ R\cos\phi\sin\phi\sin\alpha - \sin\phi(R\cos\alpha + L) \\ -R\sin\theta\cos\phi\sin\alpha + R\cos\theta\sin\phi\sin\phi\sin\alpha + \cos\theta\cos\phi(R\cos\alpha + L) \end{bmatrix}$$

As is apparent from the above equation, the visual field can be moved by the same amount of movement as that of the parallel movement of the rigid scope. Conversely, by controlling ax and ay according to the value of ψ so as to keep V constant, the target point can be continuously seen while the oblique-viewing rotation is performed as illustrated in FIG. 13. Furthermore, if the amount of change of (ax, ay) that moves to keep the position of V at a fixed position is sufficiently faster than the amount of change of (R cos ψα, R sin ψ sin α), the target does not deviate from the visual field due to the rotation of the oblique-viewing endoscope. Thus, when the oblique-viewing rotation speed is controlled as described above, the oblique-viewing can be rotated without losing the sight of the target from the screen. Further, since the relative difference between the change amounts of (R cos ψ α, R sin ψ sin α) and (ax, ay) makes an effect, the same movement can be realized by adjusting the speed of (ax, ay) in addition to the speed of the oblique-viewing rotation angle. Such a movement is limited to a case in which the trocar point is not constrained, and corresponds to, for example, a case of an oblique-viewing endoscope surgery with a small thoracotomy/small incision of the chest. Since the movement is in the Y direction, the distance between the visual field 200 and the camera is maintained.

Figure 14:
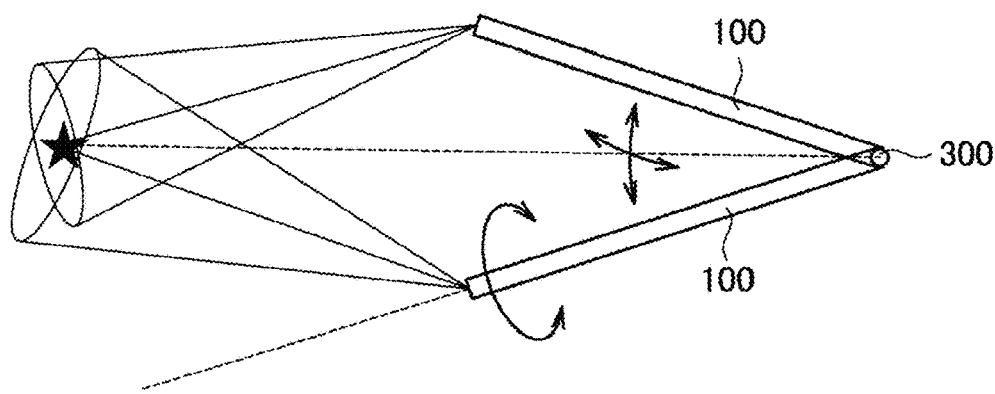
FIG. 14 is a schematic view illustrating an example of rotation about a constraint point 300.

FIG. 14 illustrates an example in which the visual field is moved up, down, left, and right by rotation about a constraint point 300. The constraint point 300 corresponds to, for example, the trocar point. In this case, the configuration of the arm can be realized with three degrees of freedom centering on the constraint point 300. Assuming that the rotation around the X axis around the constraint point 300 is set as ϕ, and the rotation around the Y axis is set as θ, each rotation matrix is as follows.

$$Rx(\phi) = \begin{bmatrix} 1 & 0 & 0 \\ 0 & \cos\phi & -\sin\phi \\ 0 & \sin\phi & \cos\phi \end{bmatrix}$$

$$Ry(\theta) = \begin{bmatrix} \cos\theta & 0 & \sin\theta \\ 0 & 1 & 0 \\ -\sin\theta & 0 & \cos\theta \end{bmatrix}$$

If θ, ϕ, and ψ are adjusted so that the above-described V is maintained, the visual field does not deviate. When the oblique-viewing angle ψ as a target is determined, the target values of θ and ϕ for maintaining the value of V are selected. When θ, ϕ, and ψ are controlled with this target value as a command value, by adjusting the oblique-viewing rotation angle described above, it is possible to control the target value without removing the target from the visual field even in the process of following the target value.

In addition, since the amount of change of V with respect to the change of θ and ϕ also changes depending on the posture of ψ, the rotation speeds of θ and ϕ may be adjusted so that the amounts of change of X and Y become the same according to the value of the oblique-viewing rotation angle ψ. Incidentally, the above calculation becomes complicated. Thus, for simple mounting, it may be set that α=0, ψ=0, and the rigid scope axis may be rotated by θ and ϕ regardless of the oblique-viewing rotation angle to simplify the movement of the visual field.

[Control of Arm that Moves Observation Target to Screen Center]

In the following, an example will be described in which the following is performed such that the observation target 210 is positioned at the center of the visual field 200 when the oblique-viewing endoscope 100 is moved around the constraint point 300. An arm control method of recognizing the position of the target in the screen by image recognition or the like and moving the observation target in the screen based on the information may be used. In addition, it is also possible to determine an operator's observation target point by gaze detection and move the observation target point to the center of the visual field.

According to this embodiment, an information processing device is provided which includes a control unit that controls the support arm device and moves the endoscope such that the target inside the body of the patient matches the optical axis of the endoscope attached to the support arm device and inserted into the body of the patient. When the target is recognized by image recognition or the like, and the arm is controlled such that the target is displayed at the screen center, a surgical instrument or a target such as tumor can be captured at the center of the image obtained by the endoscope, so as to improve the convenience of the operator. Such an information processing device may be configured separately from the endoscopic surgery system 5000, or may be configured as an arbitrary device included in the endoscopic surgery system 5000.

Hereinafter, an outline of this embodiment will be described with reference to FIGS. 15 and 16.

Figure 15:
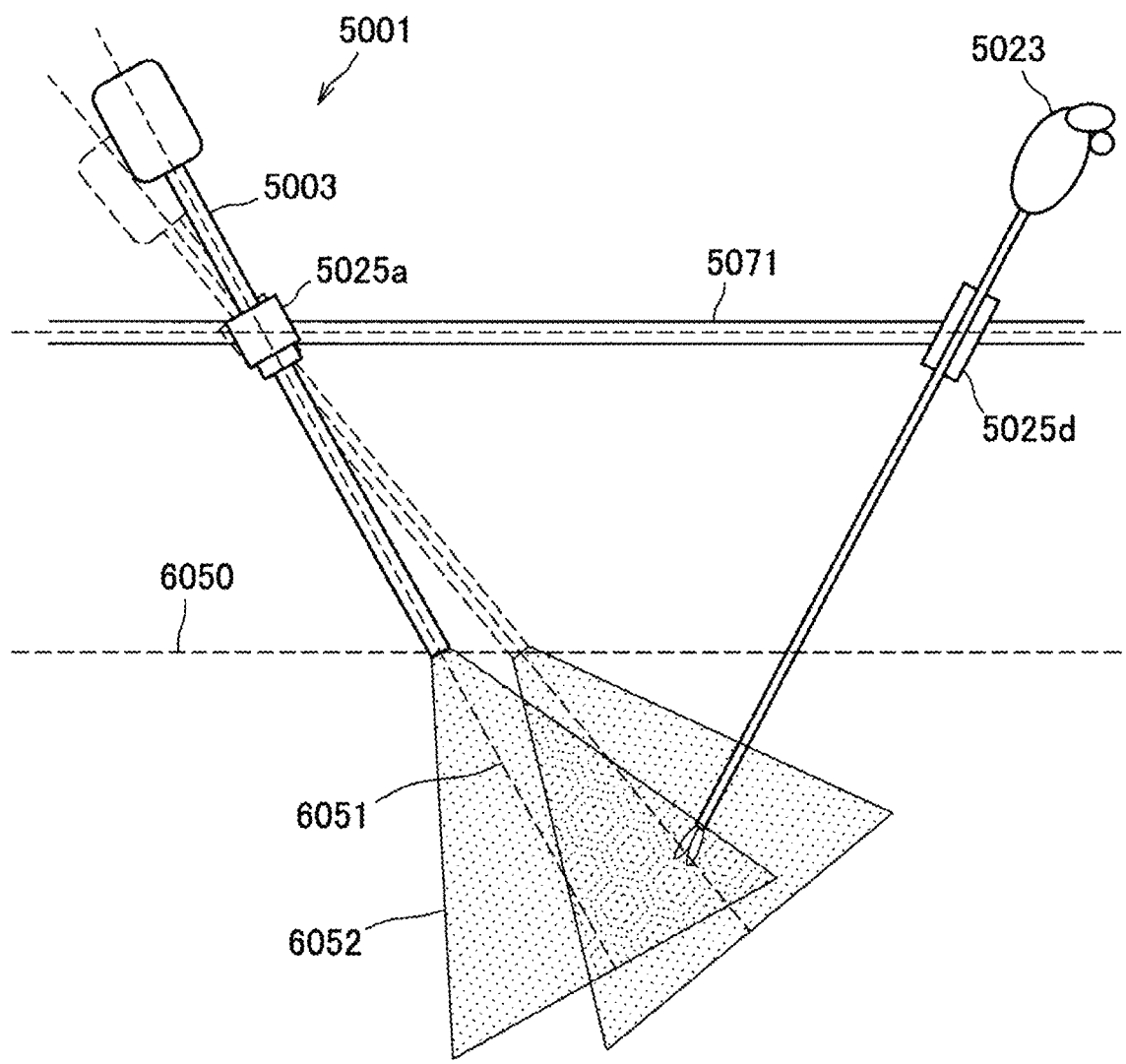
FIG. 15 is a diagram for explaining control of an arm for moving the observation target to the screen center.
Figure 16:
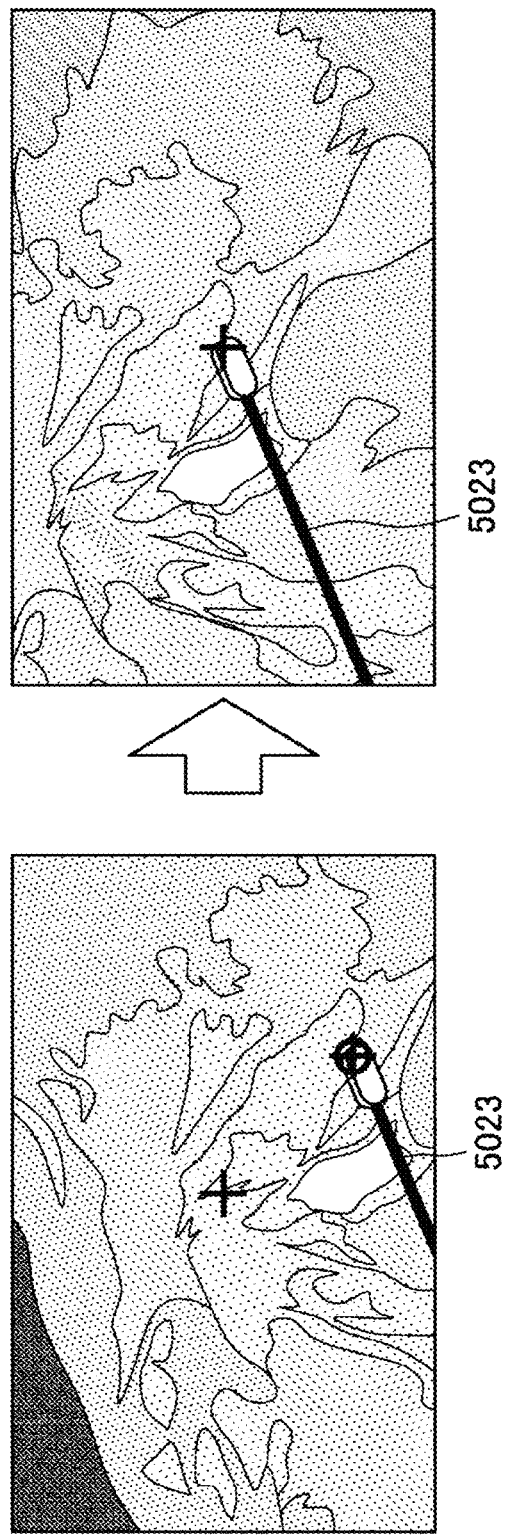
FIG. 16 is a diagram for explaining control of the arm for moving the observation target to the screen center.

FIG. 15 and FIG. 16 are diagrams for explaining the outline of this embodiment. FIG. 15 illustrates an aspect where the lens barrel 5003 of the endoscope 5001 is inserted into the body cavity of the patient 5071 from the trocar 5025a punctured in the abdominal wall of the patient 5071. The endoscope 5001 indicated by the solid line shows the current position and posture, and the endoscope 5001 indicated by the broken line shows (that is, future) the position and posture of the destination of the movement by the endoscope control process according to this embodiment. Further, the forceps 5023 is inserted from the trocar 5025d punctured in the abdominal wall of the patient 5071. In FIG. 16, the image (hereinafter, also referred to as an endoscope image) obtained by the endoscope 5001 illustrated in FIG. 15 is illustrated. The left drawing is the image obtained at the current position and posture, and the right drawing is the image obtained after the movement by the endoscope control process according to this embodiment.

Referring to FIG. 15, at the current position and posture of the endoscope 5001, the tip of the forceps 5023 is captured in the visual field 6052 of the endoscope 5001 but is not on the central axis (that is, the optical axis) 6051. Therefore, as illustrated in the left diagram of FIG. 16, an endoscope image is obtained in which the tip of the forceps 5023 is not displayed at the center. In such a situation, the endoscopic surgery system 5000 according to this embodiment performs a process of moving the endoscope 5001 so that the surgical tool such as the forceps 5023 is displayed at the screen center. Specifically, the endoscopic surgery system 5000 moves the endoscope 5001 by the support arm device 5027 (not illustrated) so that the tip of the forceps 5023 is positioned on the central axis 6051. As a result, as illustrated in the right diagram of FIG. 16, an endoscope image is obtained in which the tip of the forceps 5023 is displayed at the center. In the following, an example is illustrated in which the tip of the forceps 5023 is positioned on the central axis 6051 without considering the oblique-viewing angle and the oblique-viewing rotation angle. However, the control of the oblique-viewing endoscope 200 can be performed in consideration with the oblique-viewing angle and the oblique-viewing rotation angle. In addition, an example in which the tip of the forceps 5023 is positioned on the central axis 6051 is illustrated. However, the same is performed also in a case where the observation target 210 as a target is positioned on the central axis 6051 by performing image recognition on the observation target 210.

As described above, the endoscopic surgery system 5000 can provide an endoscope image in which the surgical tool is displayed at the screen center by automatically following the surgical tool. Therefore, the operator can continue the surgery comfortably without operating the endoscope 5001.

<2.4. Configuration Example of Control Unit for Oblique-Viewing Rotation Operation and Follow-Up Operation>

Figure 21:
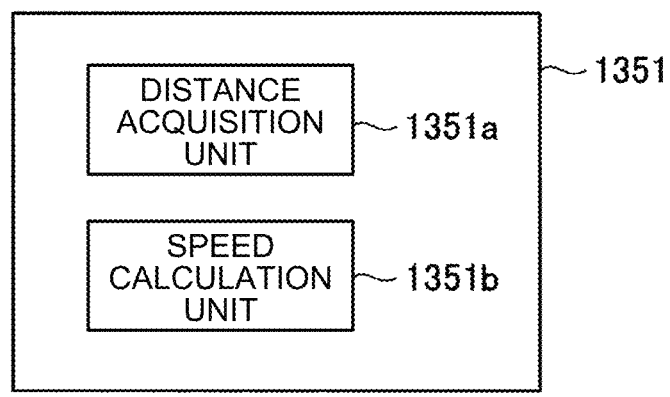
FIG. 21 is a schematic view illustrating a configuration of a control unit of a support arm device for performing an oblique-viewing rotation operation and a follow-up operation.

FIG. 21 is a schematic view illustrating the configuration of the control unit 1351 of the support arm device 1400 for performing the above-described oblique-viewing rotation operation and follow-up operation. As illustrated in FIG. 21, the control unit 1351 includes a distance acquisition unit 1351a that acquires a distance from the center of the visual field to the position of the observation target 210 in the visual field 200 obtained by imaging the observation target 210 and a speed calculation unit 1351b that calculates the speed of the oblique-viewing rotation of the oblique-viewing endoscope 100 or the moving speed of the oblique-viewing endoscope 100 based on the distance from the center of the visual field to the position of the observation target 210. The acquisition of the distance from the center of the visual field to the position of the observation target 210 by the distance acquisition unit 1351a is performed based on the result of the image recognition of the observation target 210 by the control unit 5063 of the CCU 5039.

Further, the control unit 1351 controls the support arm device 1400 such that the observation target 210 is positioned at the center of the visual field 200, based on the result of the image recognition of the observation target 210 by the control unit 5063 of the CCU 5039. At this time, the control unit 1351 controls at least one of the speed of the oblique-viewing rotation of the oblique-viewing endoscope 100 and the moving speed of the oblique-viewing endoscope 100 according to the position of the observation target 210 in the visual field 200. The control unit 1351 controls the rotation angle and the rotation speed around the long axis of the oblique-viewing endoscope 100 according to the position of the observation target 210 in the visual field 200. As described above, the control unit 5063 of the CCU 5039 can recognize the feature of the image of the observation target 210 and the position in the visual field 200 using various image recognition techniques. The control unit 1351 obtains information on the position of the observation target 210 in the visual field 200 from the CCU 5039.

The operator can specify the observation target 210 from the operation site displayed on the display device 5041 by operating the input device 5047 while viewing the image of the operation site displayed on the display device 5041 in real time. The control unit 5063 recognizes the characteristics of the image of the observation target 210 and the position in the visual field 200 based on the specified observation target 210.

<2.5. Details of Follow-Up Operation>

Next, a process for realizing the above-described endoscope control will be described with reference to FIG. 17.

Figure 17:
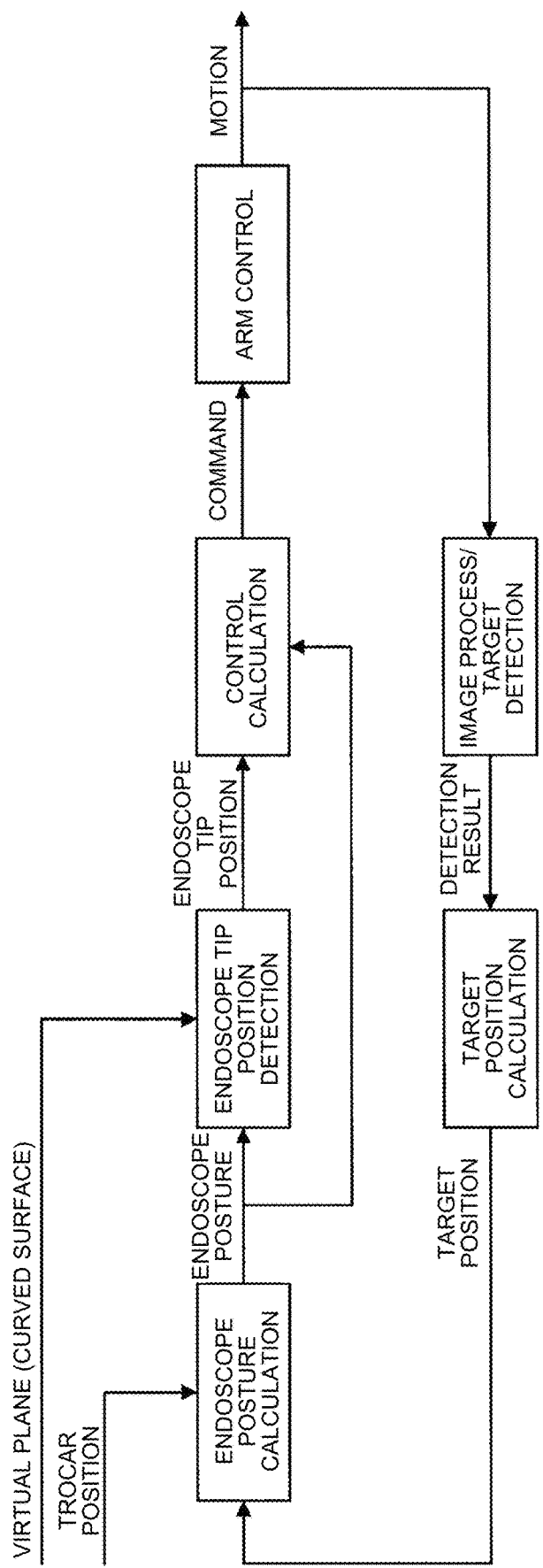
FIG. 17 is a diagram for explaining an outline of a control process for moving the observation target to the screen center.

FIG. 17 is a diagram for explaining the outline of the endoscope control process according to this embodiment. Each block illustrated in FIG. 17 indicates a process, and the endoscope control process includes a plurality of processes. As illustrated in FIG. 17, the endoscopic surgery system 5000 performs an image process to detect a target such as a surgical tool. Next, the endoscopic surgery system 5000 calculates the position of the target based on the detection result. Next, the endoscopic surgery system 5000 calculates the current posture of the endoscope based on the calculated target position and trocar position. Next, the endoscopic surgery system 5000 calculates the target endoscope tip position based on the calculated current posture of the endoscope and the setting information of the virtual plane (plane or curved surface). Next, the endoscopic surgery system 5000 calculates the amount of change in the posture of the endoscope based on the current posture of the endoscope and the target endoscope tip position, and generates control information (that is, a command) of the arm for realizing the posture change according to the calculated change amount. Then, the endoscopic surgery system 5000 controls the support arm (for example, the arm unit 5031) to operate according to the generated command. The endoscopic surgery system 5000 repeatedly performs a series of processes described above.

Hereinafter, the endoscope control processing according to this embodiment will be described in detail.

(1) First

According to this embodiment, the endoscopic surgery system 5000 can realize a function of recognizing a surgical tool from an endoscope image and automatically following the surgical instrument. Hereinafter, a calculation method will be described in which the arm operates the endoscope from the image processing portion (marker detection) and the detection result to move the surgical tool to the screen center while considering the trocar point.

Hereinafter, after the functional requirements are described, a method is described which detects the surgical tool (marker) by the image process, and then a calculation method is described which converts the detection result to the target movement information and posture information to operate.

Here, an example is described in which the arm is moved about the constraint point without considering the oblique-viewing angle and the oblique-viewing rotation angle.

(2) Image Process

The endoscopic surgery system 5000 detects a surgical tool (for example, a tip position and/or a posture of the surgical tool) by an image process.

For example, when a marker serving as a mark is attached to the tip of the surgical tool, the position of the surgical tool may be detected by the image process based on the endoscope image. It is desirable that the marker is easy to detect. For example, the marker may be a color such as blue or green that stands out as compared with the color of the organ or blood vessel in the body cavity (for example, a color positioned on the opposite side of the color of the organ or blood vessel in the hue circle). Further, the marker may be a specific pattern such as a two-dimensional code or a barcode.

For example, when a marker serving as a marker is attached to a portion of the surgical tool that is outside the body, the position of the surgical tool may be detected based on the detection result of the marker by an external sensor and the information on the length and posture of the surgical tool, and the like.

The detection of the surgical tool may be performed by a method other than the image process.

For example, by creating a special trocar, the position of the surgical tool may be calculated based on the insertion amount of the surgical tool and the angle of the trocar.

For example, when the surgical tool is attached to a support arm device different from the endoscope, the position of the surgical tool may be calculated from the position and posture information of the support arm device.

(3) Target Calculation

The endoscopic surgery system 5000 performs target calculation. The target calculation is a calculation for instructing the movement by calculating two of the position and the posture.

Specifically, the endoscopic surgery system 5000 first obtains the target position from the image processing result, and then determines the amount of change in the posture based on the current posture starting from the trocar point and the posture at the time of reaching the target position. In addition, the endoscopic surgery system 5000 performs target calculation based on the current position and posture obtained from the encoder while obtaining the movement amount from the result of the image process. However, when an actual command is issued, a finally executed command value is added with the calculated value. The reason for this is that a deviation caused by a control error occurs between the current value and the command value, and when a goal is set with the present value as a starting point when the command value is issued, the operation is not smooth and the error becomes large.

Hereinafter, an example of the flow of the target calculation process will be described with reference to FIG. 18.

Figure 18:
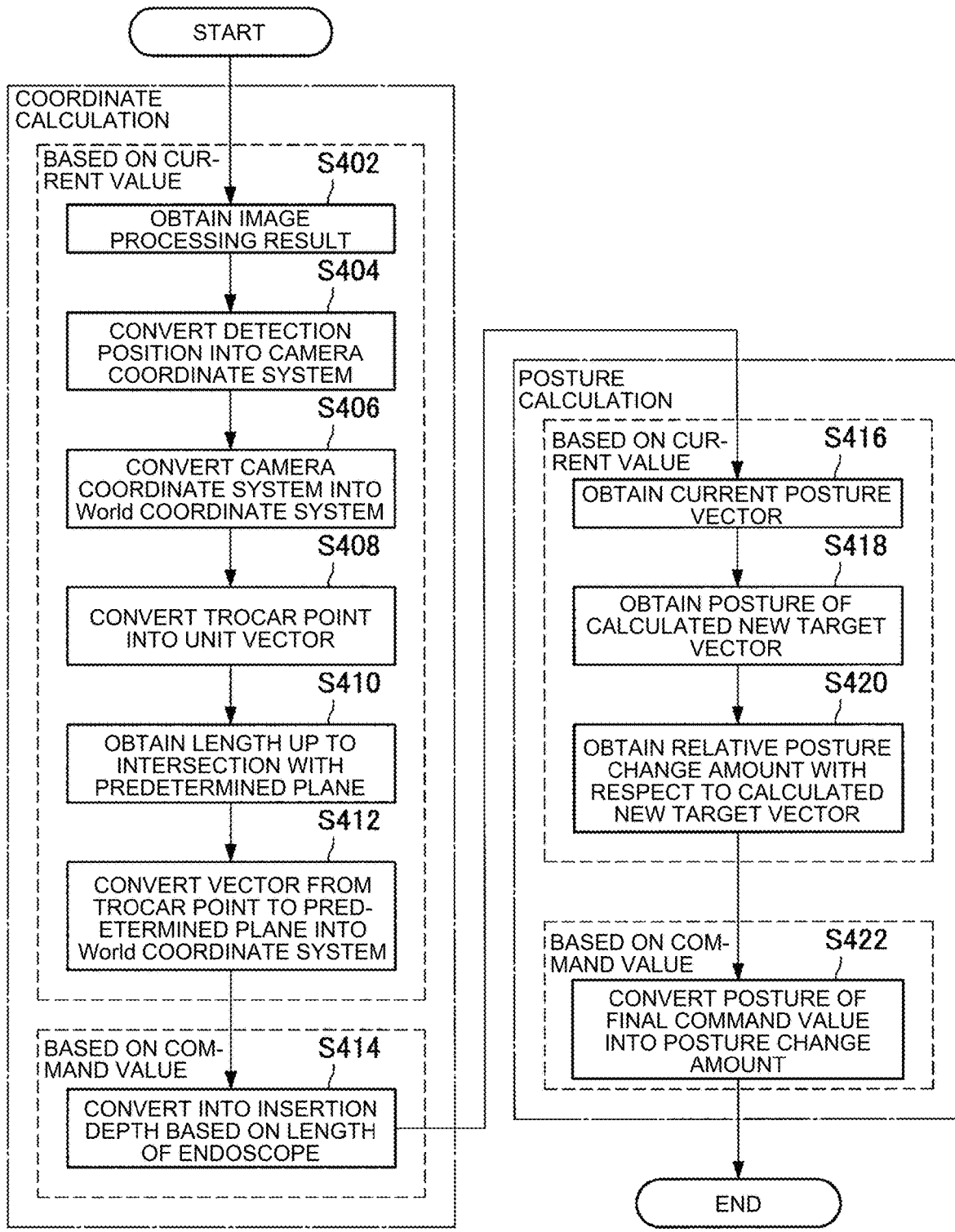
FIG. 18 is a flowchart illustrating an example of a flow of a target calculation process.

FIG. 18 is a flowchart illustrating an example of the flow of the target calculation process by the endoscopic surgery system 5000 according to this embodiment. As illustrated in FIG. 18, the endoscopic surgery system 5000 first performs coordinate calculation.

In the coordinate calculation, the endoscopic surgery system 5000 first calculates the coordinates based on the current value. Specifically, the endoscopic surgery system 5000 obtains an image processing result (Step S402). Next, the endoscopic surgery system 5000 converts the detection position into the camera coordinate system (that is, conversion from 2D to 3D) (Step S404). Next, the endoscopic surgery system 5000 converts the camera coordinate system into the World coordinate system (Step S406). Next, the endoscopic surgery system 5000 converts the trocar points into unit vectors (Step S408). Next, the endoscopic surgery system 5000 obtains the length up to the intersection with a predetermined plane (that is, a virtual plane) (Step S410). Next, the endoscopic surgery system 5000 converts the vector from the trocar point to the predetermined plane into the World coordinate system (Step S412).

After calculating the coordinates based on the current value, the endoscopic surgery system 5000 calculates the coordinates based on the command value. Specifically, the endoscopic surgery system 5000 performs conversion into the insertion depth based on the length of the endoscope (Step S414).

After the coordinate calculation, the endoscopic surgery system 5000 performs posture calculation.

In the posture calculation, the endoscopic surgery system 5000 first calculates the posture based on the current value. Specifically, the endoscopic surgery system 5000 obtains the current posture vector (Step S416). Next, the endoscopic surgery system 5000 obtains the posture of the calculated new target vector (Step S418). Next, the endoscopic surgery system 5000 obtains a relative posture change amount with respect to the calculated new target vector (Step S420).

After calculating the posture based on the current value, the endoscopic surgery system 5000 calculates the posture based on the command value. Specifically, the endoscopic surgery system 5000 converts the posture of the final command value into a posture change amount (Step S422).

Through the process described above, the endoscopic surgery system 5000 obtains the target position and the target posture.

(4) Target Position Calculation

Figure 19:
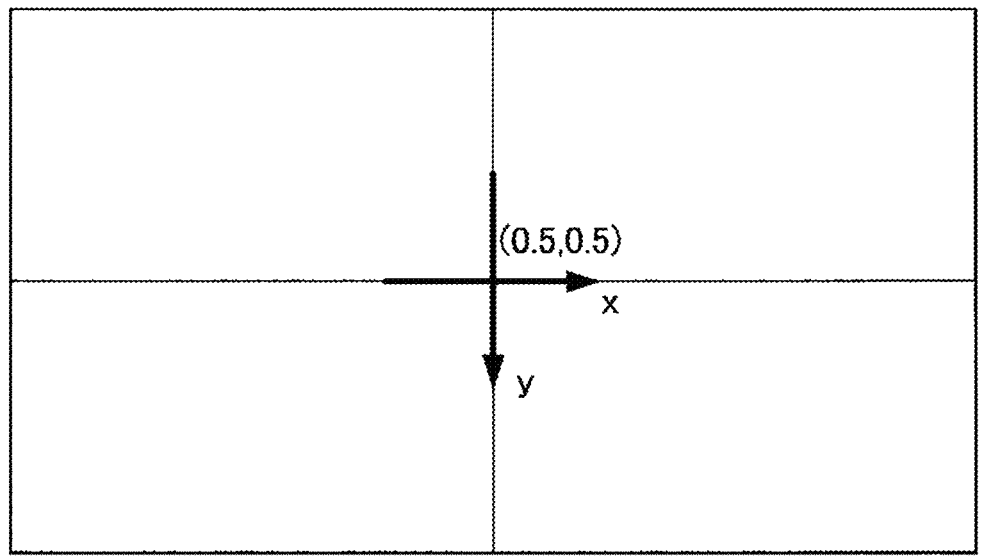
FIG. 19 is a diagram for explaining target position calculation.

FIG. 19 is a diagram for explaining target position calculation according to this embodiment. As illustrated in FIG. 19, the image processing result is notified as values in which the position as viewed from the camera coordinate system with the screen center at the tip of the camera set as (0.5, 0.5) is normalized to [0.0 to 1.0]. As it is a dimensionless value as it is, the endoscopic surgery system 5000 first performs conversion to a metric system. However, since the image processing result is 2D and has no information on the depth direction, the endoscopic surgery system 5000 assumes that the depth is, for example, 50 [mm] at the time of conversion, and obtains a virtual position by combination with a field angle.

The reason why the depth is assumed to be 50 [mm] is described. The first reason is that, when the assumed value is larger than the actual value, the moving amount of (x, y) becomes larger than the actual (x, y), and overruns (oscillates). The second reason is that the shortest distance is set by setting the photographing distance in the assumed method to 50 [mm] to 100 [mm]. The third reason is that when the actual distance is large, the movement is newly determined from the residual based on the next image processing result, so that the goal can be finally reached.

(5) Target Posture Calculation

The endoscopic surgery system 5000 obtains a target posture after a target position is determined. The control unit 1351 controls the arm unit 1420 by the arm unit based on the target position and the target posture.

<2.6. Specific Example of Follow-Up Operation>

Figure 20A:
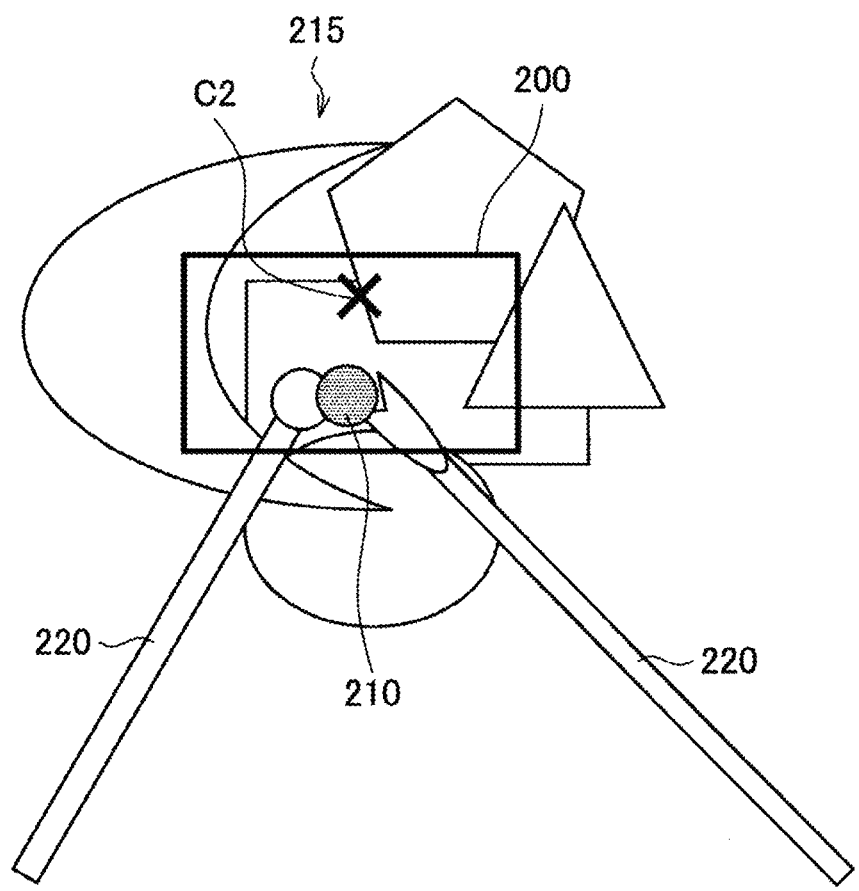
FIG. 20A is a schematic view for explaining a specific example in a case where an oblique-viewing is directed to the left according to the control of the oblique-viewing endoscope according to this embodiment.
Figure 20B:
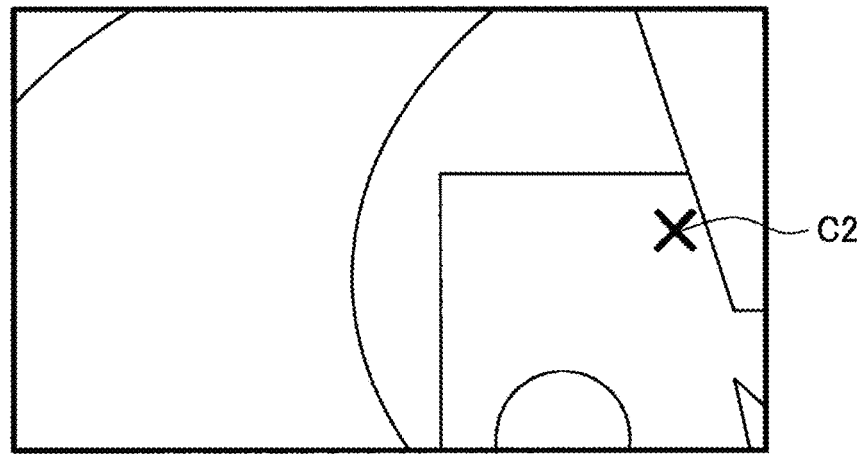
FIG. 20B is a schematic view for explaining a specific example in a case where the oblique-viewing is directed to the left according to the control of the oblique-viewing endoscope according to this embodiment.
Figure 20C:
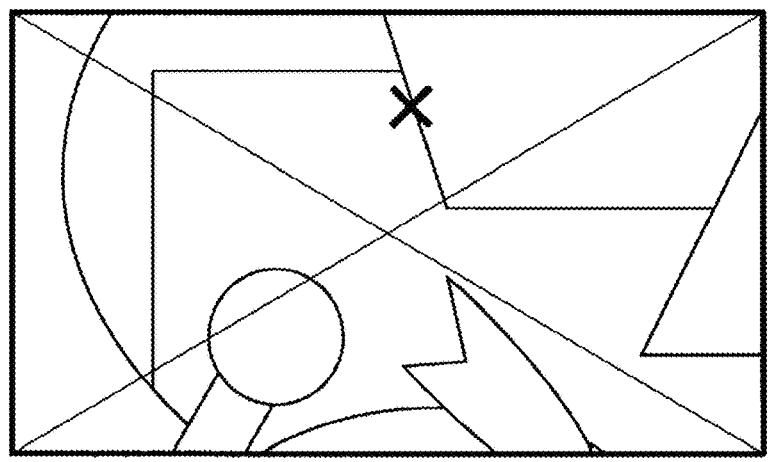
FIG. 20C is a schematic view for explaining a specific example in a case where the oblique-viewing is directed to the left according to the control of the oblique-viewing endoscope according to this embodiment.

FIGS. 20A to 20D are schematic views for explaining a specific example in a case where an oblique-viewing is directed to the left according to the control of the oblique-viewing endoscope according to this embodiment. Similarly to FIG. 7, FIGS. 20A to 20D also illustrates a state in which an observation target 210 to be viewed by a user (operator) exists in various organs 215. Here, FIG. 20A illustrates a state (a state under the oblique-viewing) in which the optical axis of the objective optical system is directed to the lower side (the side of the operator who operates the surgical tool 220) of the visual field 200 with respect to the position of the scope axis C. FIG. 20B illustrates an enlarged visual field 200 of FIG. 20A. In this case, when the oblique-viewing rotation is performed to view the left side of the visual field 200, in the existing technology in which the follow-up operation to the observation target 210 is not performed as illustrated in FIG. 20C, the left side of the observation target 210 can be observed by the oblique-viewing rotation compared to FIG. 20B, but the observation target 210 cannot be viewed.

Figure 20D:
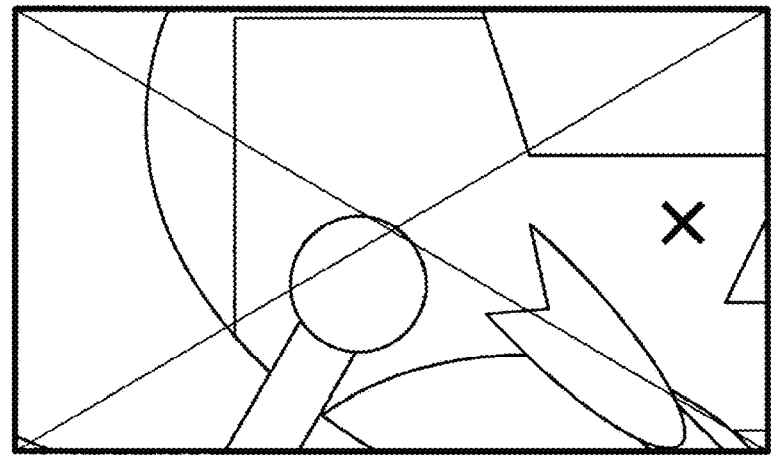
FIG. 20D is a schematic view for explaining a specific example in a case where the oblique-viewing is directed to the left according to the control of the oblique-viewing endoscope according to this embodiment.

On the other hand, in this embodiment, as illustrated in FIG. 20D, the arm is controlled so as to follow the observation target 210, such that the observation target 210 is positioned at the screen center. Thus, the oblique-viewing endoscope 100 can be rotated to the left without losing the sight of the observation target 210.

<<3. Example in Which Holding Unit for Independently Controlling Rotation of Oblique-Viewing Endoscope is Provided>>

In the configuration example illustrated in FIG. 3 described above, an example is illustrated in which the posture and position of the oblique-viewing endoscope 100 are changed only by controlling the active joints 1421a to 1421f of the arm unit 1420. On the other hand, a holding unit with a built-in actuator for independently controlling the rotation of the oblique-viewing endoscope may be provided at the tip of the arm unit 1420. In this case, the rotation of the oblique-viewing endoscope 100 is performed by the holding unit, and the position of the entire oblique-viewing endoscope and the posture with respect to the operation site can be controlled by the active joint of the arm.

Figure 22:
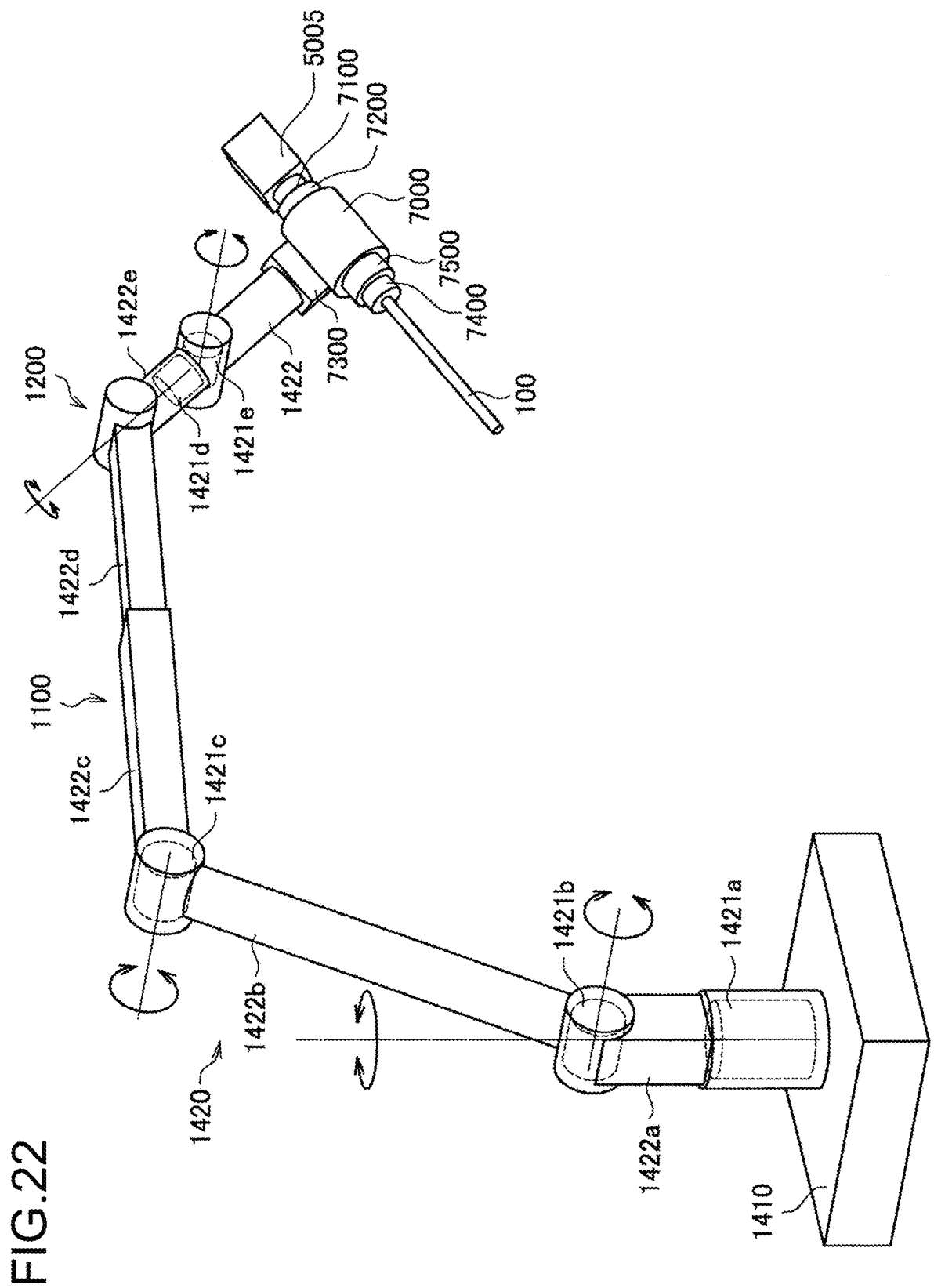
FIG. 22 is a schematic view illustrating a configuration in which a holding unit that independently controls the rotation of the oblique-viewing endoscope and the rotation of a camera head is provided at the tip of an arm unit in the configuration example illustrated in FIG. 3.

FIG. 22 is a schematic view illustrating a configuration in which a holding unit 7000 that independently controls the rotation of the oblique-viewing endoscope 100 and the rotation of a camera head 7100 is provided at the tip of an arm unit 1420 in the configuration example illustrated in FIG. 3. The holding unit 7000 is mounted to an endoscope unit mounting unit 7300 at the tip of the arm unit 1420, and includes a camera head mounting unit 7100, a camera head rotation drive unit 7200, an oblique-viewing endoscope mounting unit 7400, and an oblique-viewing endoscope rotation drive unit 7500.

As illustrated in FIG. 22, the camera head 5005 is mounted on the camera head rotation drive unit 7200 via the camera head mounting unit 7100. The camera head rotation drive unit 7200 includes an actuator 7210 such as a motor, and rotates the camera head 5005 with respect to the endoscope unit mounting unit 7300 and the main body of the holding unit 7000.

Further, the oblique-viewing endoscope 100 is mounted to the oblique-viewing endoscope rotation drive unit 7500 via the oblique-viewing endoscope mounting unit 7400. The oblique-viewing endoscope rotation drive unit 7500 includes an actuator 7510 such as a motor, and rotates the oblique-viewing endoscope 100 around the endoscope unit mounting unit 7300 and the main body of the holding unit 7000.

Figure 23:
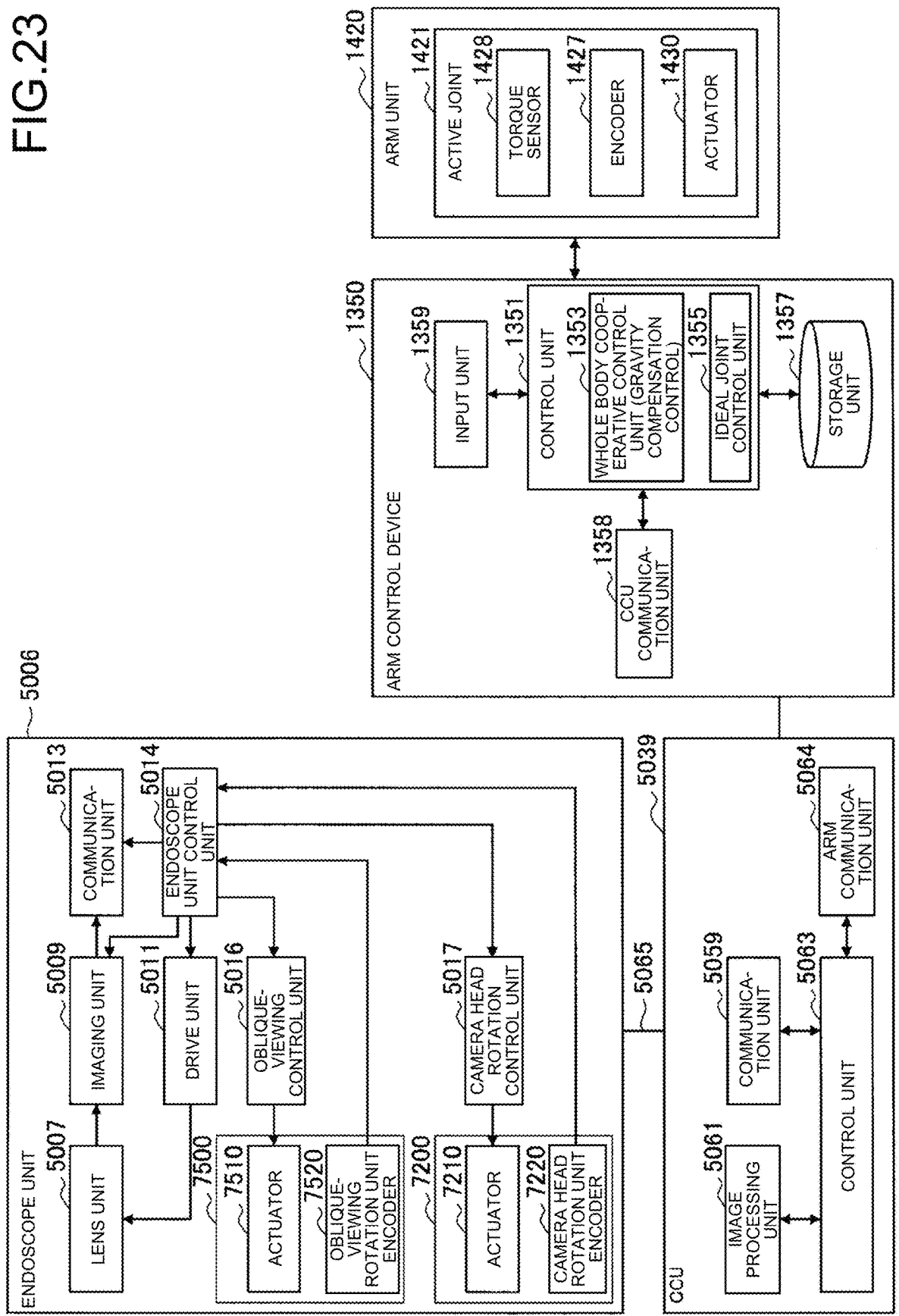
FIG. 23 is a schematic view illustrating a configuration of a support arm device including an arm unit and a control device, an endoscope unit, and a CCU in the configuration example illustrated in FIG. 22.

FIG. 23 is a schematic view illustrating the configuration of the support arm device 1400 including the arm unit 1420 and the control device 1350, an endoscope unit 5006, and a CCU 5039 in the configuration example illustrated in FIG. 22. The control device 1350 includes a CCU communication unit 1358 that performs communication with the CCU 5039 in addition to the configuration illustrated in FIG. 4. The CCU 5039 includes an arm communication unit 5064 that performs communication with the control device 1350 in addition to the configuration illustrated in FIG. 2. The control device 1350 and the CCU 5039 can transmit and receive information to and from each other by the communication between the CCU communication unit 1358 and the arm communication unit 5064. Further, the endoscope unit 5006 is obtained by adding the function of the holding unit 7000 to the camera head 5005 illustrated in FIG. 2, and includes an endoscope unit control unit 5014 instead of the control unit 5015 illustrated in FIG. 2. In addition to the configuration of the camera head 5005 illustrated in FIG. 2, the endoscope unit 5006 includes an oblique-viewing control unit (first control unit) 5016, a camera head control unit (second control unit) 5017, an oblique-viewing endoscope rotation drive unit 7500, and a camera head rotation drive unit 7200. The oblique-viewing control unit 5016 and the camera head control unit 5017 may be provided in the holding unit 7000. The functions of the endoscope unit control unit 5014, the oblique-viewing control unit 5016, and the camera head control unit 5017 may be provided in the control unit 1351 of the control device 1350.

The oblique-viewing control unit 5016 drives the actuator 7510 based on the command from the endoscope unit control unit 5014. The actuator 7510 and the oblique-viewing rotation unit encoder 7520 are provided in the oblique-viewing endoscope rotation drive unit 7500. The endoscope unit control unit 5014 drives the actuator 7510 and controls the rotation of the oblique-viewing endoscope 100 around the axis based on the rotation angle of the actuator 7510 detected by the oblique-viewing rotation unit encoder 7520.

Further, the camera head control unit 5017 drives the actuator 7210 based on the command from the endoscope unit control unit 5014. The actuator 7210 and the camera head rotation unit encoder 7220 are provided in the camera head rotation drive unit 7200. The endoscope unit control unit 5014 controls the rotation of the camera head 5005 around the axis based on the rotation angle of the actuator 7210 detected by the camera head rotation unit encoder 7220.

With the above configuration, the oblique-viewing endoscope 100 and the camera head 5005 can rotate independently with respect to the endoscope unit mounting unit 7300. Accordingly, it becomes possible to rotate the oblique-viewing endoscope 100 to visually recognize a desired observation target and to rotate the camera head 5005 to appropriately control the top and bottom of the image.

Figure 24:
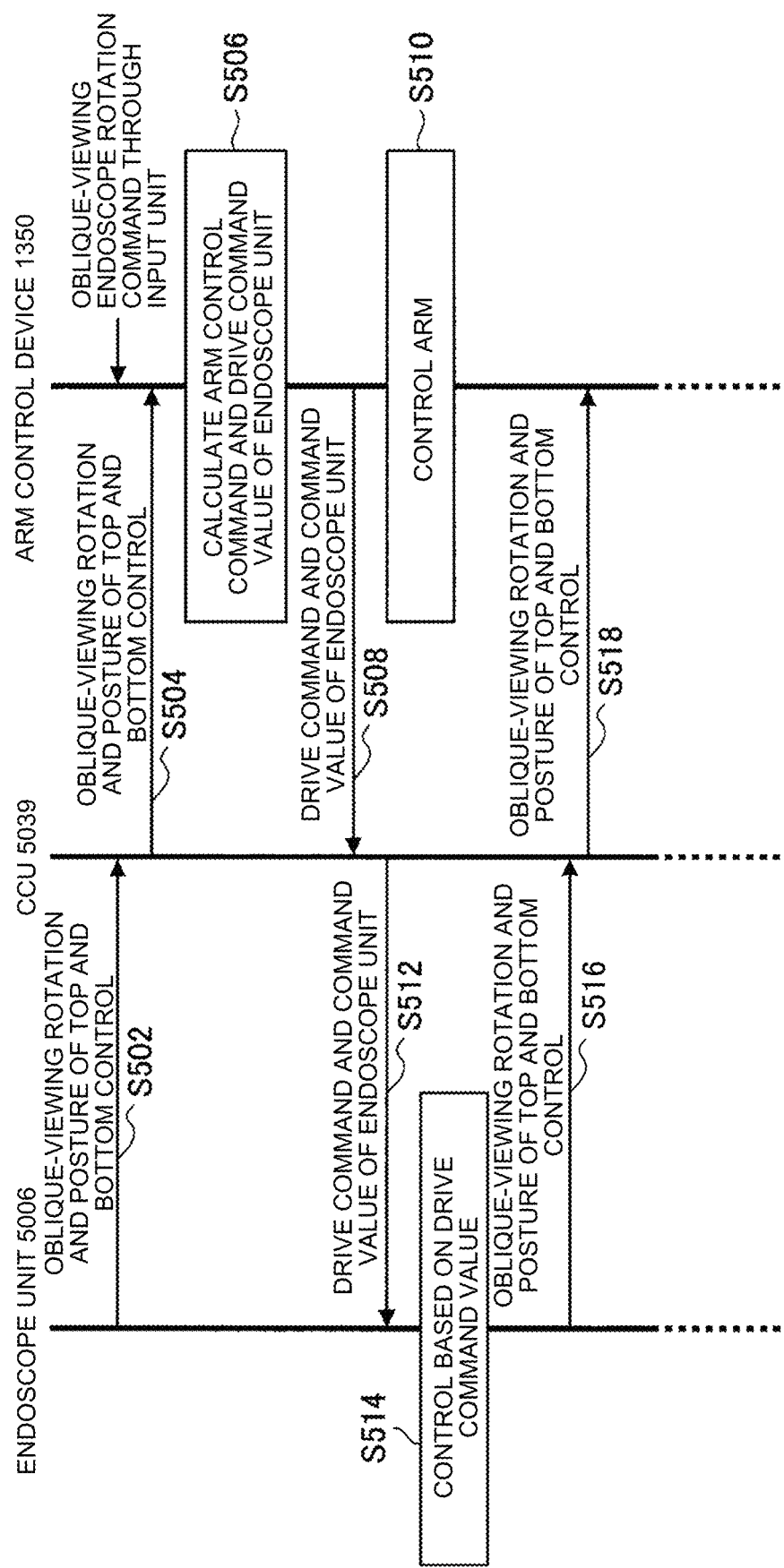
FIG. 24 is a sequence diagram illustrating a processing flow in the configuration illustrated in FIGS. 22 and 23.

FIG. 24 is a sequence diagram illustrating a processing flow in the configuration illustrated in FIGS. 22 and 23. First, in Step S502, the information on the oblique-viewing rotation of the oblique-viewing endoscope 100 and the posture of the camera head 5005 for top and bottom control is sent from the endoscope unit to the CCU 5039. In the next Step S504, the information on the oblique-viewing rotation of the oblique-viewing endoscope 100 and the posture of the camera head 5005 for the top and bottom control is sent from the CCU 5039 to the arm control device.

In the next Step S506, an arm control command and a drive command value of the endoscope unit are calculated. In the next Step S508, the drive command value of the endoscope unit is sent from the arm control device to the CCU 5039 together with the drive command. In Step S510, the arm is controlled based on the arm control command.

In Step S512, the drive command value of the endoscope unit is sent from the CCU 5039 to the endoscope unit together with the drive command. In the next Step S514, the endoscope unit is controlled based on the drive command value.

In the next Step S516, the information on the oblique-viewing rotation of the oblique-viewing endoscope 100 and the posture of the camera head 5005 for top and bottom control is sent from the endoscope unit to the CCU 5039. In the next Step S504, the information on the oblique-viewing rotation of the oblique-viewing endoscope 100 and the posture of the camera head 5005 for the top and bottom control is sent from the CCU 5039 to the arm control device.

In the next Step S510,

<<4. Summary>>

As described above, according to this embodiment, the speed of the oblique-viewing rotation decreases as the distance from the center of the visual field 200 of the monitor increases. Thus, it is possible to suppress the observation target 210 from deviating from the visual field 200 in the case of the visual recognition of the periphery by using oblique-viewing rotation of the oblique-viewing endoscope 100.

Further, according to this embodiment, the image of the observation target 210 existing inside the human body of the patient is recognized, the medical arm is controlled so that the optical axis of the objective optical system of the oblique-viewing endoscope 100 matches the position of an observation target 210, and the endoscope is moved while the tip of the endoscope is constrained on the virtual plane. Accordingly, when the oblique-viewing rotation is performed, the observation target 210 such as a surgical instrument or a tumor can be captured at the center of the visual field 200, and the convenience for the operator is improved.

Therefore, the operator can perform the oblique-viewing rotation while always keeping a desired part, an instrument, and the like in the screen, and can suppress that the sight of the observation target 210 is lost due to the oblique-viewing rotation. Further, the realization can be easily made without performing the posture control based on the distance information as in the pivot operation around the subject.

The preferred embodiments of the present disclosure have been described above in detail with reference to the accompanying drawings, but the technical scope of the present disclosure is not limited to such examples. It is obvious that a person with ordinary knowledge in the art to which the present disclosure pertains can come up with various changes or modifications within the scope of the technical idea described in the claims. Of course, it is understood that they belong to the technical scope of the present disclosure.

Note that a series of processes by each device described in this specification may be realized using any of software, hardware, and a combination of software and hardware. A program constituting the software is stored in advance in a storage medium (non-transitory medium) provided inside or outside each device, for example. Each program is read into a RAM when the computer executes the program, and is executed by a processor such as a CPU.

Further, the processes described with reference to the flowcharts and the like in this specification do not necessarily have to be executed in the illustrated order. Some processing Steps may be performed in parallel. Further, additional processing Steps may be employed, and some processing Steps may be omitted.

Further, the effects described in this specification are merely illustrative or exemplary and are not limited. That is, the technology according to the present disclosure can exhibit other effects that are apparent to those skilled in the art from the description of this specification in addition to or instead of the above effects.

Note that the following configurations also belong to the technical scope of the present disclosure.

(1)

A surgical arm system comprising:

an articulated arm in which a plurality of joints is rotatably connected by a plurality of links and which is capable of supporting an oblique-viewing endoscope at a tip; and a control system which controls the articulated arm to change a position and a posture of the oblique-viewing endoscope, wherein the control system controls at least one of a rotation speed and a movement speed of the oblique-viewing endoscope in a visual field imaged through the oblique-viewing endoscope based on a position of an observation target in the visual field.

(2)

The surgical arm system according to (1), wherein the control system controls a rotation angle and a rotation speed of the oblique-viewing endoscope around a long axis.

(3)

The surgical arm system according to (1) or (2), wherein the control system controls a posture and a moving speed of the articulated arm so as to move a position of the observation target within the visual field.

(4)

The surgical arm system according to any one of (1) to (3), wherein the control system controls at least one of a rotation speed and a movement speed of the oblique-viewing endoscope in the visual field based on a distance from a center of the visual field to a position of the observation target.

(5)

The surgical arm system according to any one of (1) to (4), wherein the control system reduces the rotation speed as the distance from the center of the visual field to the position of the observation target increases.

(6)

The surgical arm system according to any one of (1) to (5), wherein the control system controls, based on a result of determining the position of the observation target, the articulated arm which supports the oblique-viewing endoscope such that the observation target is positioned at the center of the visual field.

(7)

The surgical arm system according to (6), wherein the control system controls, based on a result of image recognition of the observation target, the articulated arm which supports the oblique-viewing endoscope such that the observation target is positioned at the center of the visual field.

(8)

The surgical arm system according to any one of (1) to (7), wherein the control system sets the rotation speed to zero in a case that the observation target is positioned at an end of the visual field.

(9)

The surgical arm system according to (5), wherein the control system controls the rotation speed such that a decrease amount of the rotation speed with respect to an increase amount of the distance has a linear relationship.

(10)

The surgical arm system according to (5), wherein in a case that the distance is within a predetermined range, the control system sets the rotation speed to be the same as the rotation speed in a case that the center matches the position of the observation target.

(11)

The surgical arm system according to (5), wherein in a case that the distance exceeds a predetermined range, the control system sets the rotation speed to a constant value.

(12)

The surgical arm system according to any one of (1) to (11), wherein the control system includes a first control unit which controls rotation of the oblique-viewing endoscope and a second control unit which controls the articulated arm.

(13)

The surgical arm system according to (12), wherein the articulated arm includes a holding unit which holds the oblique-viewing endoscope and a camera head in rotation controllable manner independently of each other.

(14)

The surgical arm system according to (13), wherein the holding unit includes the first control unit, and the second control unit obtains rotation angle information of the oblique-viewing endoscope obtained by the first control unit via an image processing unit connected to the camera head and controls the articulated arm based on the rotation angle information.

(15)

A surgical arm control system which controls an articulated arm in which a plurality of joints is rotatably connected by a plurality of links and which is capable of supporting an oblique-viewing endoscope at a tip, and controls the articulated arm to change a position and a posture of the oblique-viewing endoscope, wherein at least one of a rotation speed and a movement speed of the oblique-viewing endoscope is controlled in a visual field imaged through the oblique-viewing endoscope based on a position of an observation target in the visual field.

REFERENCE SIGNS LIST

100 OBLIQUE-VIEWING ENDOSCOPE
200 VISUAL FIELD
210 OBSERVATION TARGET
350 CONTROL DEVICE
351 CONTROL UNIT
351a DISTANCE ACQUISITION UNIT
351b SPEED CALCULATION UNIT
400 SUPPORT ARM DEVICE

The invention claimed is:

1. A surgical arm system comprising:

an articulated arm in which a plurality of joints is rotatably connected by a plurality of links and which is capable of supporting an oblique-viewing endoscope at a tip; and a control system which controls the articulated arm to change a position and a posture of the oblique-viewing endoscope, wherein the control system controls at least one of a rotation speed and a movement speed of the oblique-viewing endoscope, in a visual field imaged through the oblique-viewing endoscope, based on a position of an observation target in the visual field, wherein the control system controls a rotation angle and the rotation speed of the oblique-viewing endoscope around a long axis, wherein the control system reduces the rotation speed as the distance from the center of the visual field to the position of the observation target increases.

2. The surgical arm system according to claim 1, wherein the control system controls a posture and a moving speed of the articulated arm so as to move a position of the observation target within the visual field.

3. The surgical arm system according to claim 1, wherein the control system controls at least one of the rotation speed and the movement speed of the oblique-viewing endoscope in the visual field based on a distance from a center of the visual field to a position of the observation target.

4. The surgical arm system according to claim 1, wherein the control system controls, based on a result of determining the position of the observation target, the articulated arm which supports the oblique-viewing endoscope such that the observation target is positioned at the center of the visual field.

5. The surgical arm system according to claim 4, wherein the control system controls, based on a result of image recognition of the observation target, the articulated arm which supports the oblique-viewing endoscope such that the observation target is positioned at the center of the visual field.

6. The surgical arm system according to claim 1, wherein the control system sets the rotation speed to zero in a case that the observation target is positioned at an end of the visual field.

7. The surgical arm system according to claim 1, wherein the control system controls the rotation speed such that a decrease amount of the rotation speed with respect to an increase amount of the distance has a linear relationship.

8. The surgical arm system according to claim 1, wherein in a case that the distance is within a predetermined range, the control system sets the rotation speed to be the same as the rotation speed in a case that the center matches the position of the observation target.

9. The surgical arm system according to claim 1, wherein in a case that the distance exceeds a predetermined range, the control system sets the rotation speed to a constant value.

10. The surgical arm system according to claim 1, wherein the control system includes a first control unit which controls rotation of the oblique-viewing endoscope and a second control unit which controls the articulated arm.

11. The surgical arm system according to claim 10, wherein the articulated arm includes a holding unit which holds the oblique-viewing endoscope and a camera head in rotation controllable manner independently of each other.

12. The surgical arm system according to claim 11, wherein the holding unit includes the first control unit, and the second control unit obtains rotation angle information of the oblique-viewing endoscope obtained by the first control unit via an image processing unit connected to the camera head and controls the articulated arm based on the rotation angle information.

13. A surgical arm control system which controls an articulated arm in which a plurality of joints is rotatably connected by a plurality of links and which is capable of supporting an oblique-viewing endoscope at a tip, and controls the articulated arm to change a position and a posture of the oblique-viewing endoscope, wherein at least one of a rotation speed and a movement speed of the oblique-viewing endoscope is controlled in a visual field imaged through the oblique-viewing endoscope based on a position of an observation target in the visual field; and a rotation angle and the rotation speed of the oblique-viewing endoscope are controlled around a long axis, wherein the control system reduces the rotation speed as the distance from the center of the visual field to the position of the observation target increases.

14. The surgical arm control system according to claim 13, wherein at least one of the rotation speed and the movement speed of the oblique-viewing endoscope is controlled in the visual field based on a distance from a center of the visual field to a position of the observation target.

15. The surgical arm control system according to claim 13, wherein the rotation speed is reduced as the distance from the center of the visual field to the position of the observation target increases.

* * * * *